(12) United States Patent
Ishii et al.

(10) Patent No.: US 10,195,462 B2
(45) Date of Patent: Feb. 5, 2019

(54) RADIATION IRRADIATING APPARATUS AND RADIATION DOSE MANAGEMENT SYSTEM

(71) Applicant: TOSHIBA MEDICAL SYSTEMS CORPORATION, Otawara-Shi (JP)

(72) Inventors: Shigeyuki Ishii, Nasushiobara (JP); Takeshi Ezumi, Otawara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 138 days.

(21) Appl. No.: 14/883,930

(22) Filed: Oct. 15, 2015

(65) Prior Publication Data

US 2016/0114187 A1 Apr. 28, 2016

(30) Foreign Application Priority Data

Oct. 22, 2014 (JP) .................. 2014-215308

(51) Int. Cl.
  *A61B 6/00* (2006.01)
  *A61N 5/10* (2006.01)
(52) U.S. Cl.
  CPC ............ *A61N 5/1031* (2013.01); *A61B 6/542* (2013.01); *A61N 5/1038* (2013.01); *A61B 6/4441* (2013.01); *A61B 6/487* (2013.01); *A61B 6/566* (2013.01); *A61N 5/1067* (2013.01); *A61N 5/1071* (2013.01); *A61N 2005/1074* (2013.01)
(58) Field of Classification Search
  CPC ..................................................... A61B 6/542
  See application file for complete search history.

(56) References Cited

U.S. PATENT DOCUMENTS

| 8,611,499 B2 | 12/2013 | Spahn |
| 8,681,941 B2 | 3/2014 | Bernhardt et al. |
| 2003/0125616 A1* | 7/2003 | Black .................. A61N 5/1048 600/407 |
| 2013/0003915 A1 | 1/2013 | Lautenschlager et al. |

(Continued)

FOREIGN PATENT DOCUMENTS

| JP | 2011-234928 A | 11/2011 |
| JP | 2014-113478 | 6/2014 |

OTHER PUBLICATIONS

Japanese Office Action dated Apr. 24, 2018, issued in Japanese Patent Application No. 2014-215308.

*Primary Examiner* — Dani Fox
(74) *Attorney, Agent, or Firm* — Oblon, McClelland, Maier & Neustadt, L.L.P.

(57) ABSTRACT

A radiation irradiating apparatus includes a processing circuitry. The processing circuitry acquires a past cumulative dose distribution associated with patient identifying information, from a storage that is storable a cumulative dose distribution. The processing circuitry calculates a first cumulative dose distribution and a second cumulative dose distribution during a radiation irradiation to a patient associated with the patient identifying information, the first cumulative dose distribution being a cumulative dose distribution, the second cumulative dose distribution being generated by adding the first cumulative dose distribution to the past cumulative dose distribution. The processing circuitry displays, on a display, at least one of the first and second cumulative dose distributions during the radiation irradiation.

13 Claims, 20 Drawing Sheets

(56) References Cited

U.S. PATENT DOCUMENTS

2013/0089176 A1\* 4/2013 Nabatame ............ G01N 23/046
  378/8
2013/0182822 A1\* 7/2013 Sakaguchi ............. A61B 6/022
  378/42

\* cited by examiner

| CUMULATIVE DOSE DISTRIBUTION | PATIENT IDENTIFYING INFORMATION | EXECUTION TIME INFORMATION |
|---|---|---|
|  | P1 | 2012/07/04 |
|  | P2 | 2013/01/08 |
|  | P1 | 2013/01/22 |
|  | P1 | 2013/02/02 |
| ⋮ | ⋮ | ⋮ |

| CUMULATIVE DOSE DISTRIBUTION | PATIENT IDENTIFYING INFORMATION | EXECUTION TIME INFORMATION | APPARATUS IDENTIFYING INFORMATION |
|---|---|---|---|
|  | P1 | 2012/07/04 | RADIATION IRRADIATING APPARATUS 50a |
|  | P2 | 2013/01/08 | RADIATION IRRADIATING APPARATUS 50a |
|  | P1 | 2013/01/22 | RADIATION IRRADIATING APPARATUS 50b |
|  | P1 | 2013/02/02 | RADIATION IRRADIATING APPARATUS 50a |
| ⋮ | ⋮ | ⋮ | ⋮ |

RADIATION IRRADIATING APPARATUS AND RADIATION DOSE MANAGEMENT SYSTEM

CROSS-REFERENCE TO RELATED APPLICATION

This application is based upon and claims the benefit of priority from Japanese Patent Application No. 2014-215308, filed on Oct. 22, 2014, the entire contents of which are incorporated herein by reference.

FIELD

An embodiment as an aspect of the present invention relates to a radiation irradiating apparatus capable of displaying a cumulative dose distribution, and a radiation dose management system.

BACKGROUND

At present, the U.S., Europe and therearound perceive, as problems, increase in exposure due to radiological image examinations. Customers have a problem to reduce exposure to patients. The total dose of American citizens has increased six times as much as that in 1980. The American Association of Physicists in Medicine has warned medical doctors of not executing unnecessary radiological image examinations. American medical technologists have been educated to perform lower-dose examinations.

In recent years, a dose tracking system (DTS) has been developed that visualizes a cumulative dose (exposed dose) due to radiation irradiation during application of a radiation irradiating manipulation (an examination (imaging), therapy, surgery and the like which are accompanied by radiation irradiation) to a patient. This system sequentially (in real time) displays the cumulative dose totalized from the start of the radiation irradiating manipulation to the present time.

During application of a further radiation irradiating manipulation to a patient having already been subjected to a radiation irradiating manipulation through a conventional DTS, the total cumulative dose sometimes exceeds a threshold even though the single cumulative dose does not exceeds a threshold for a single radiation irradiating manipulation. The single cumulative dose is a cumulative dose to be sequentially calculated during the radiation irradiating manipulation under execution. The total cumulative dose is a cumulative dose calculated by adding the current, single cumulative dose to the cumulative dose due to past radiation irradiating manipulations.

Excess of the total cumulative dose above the threshold causes a possibility of following occurrence of erythema on the skin of a patient, which is radiodermatitis.

There is a problem in that displaying only one of the single cumulative dose and the total cumulative dose is insufficient to monitor the cumulative doses during execution of a radiation irradiating manipulation. However, this problem itself has not been identified from a conventional viewpoint. Consequently, there is no technique to effectively display both of the single cumulative dose and the total cumulative dose.

BRIEF DESCRIPTION OF THE DRAWINGS

In accompanying drawings.

Figure 17A:
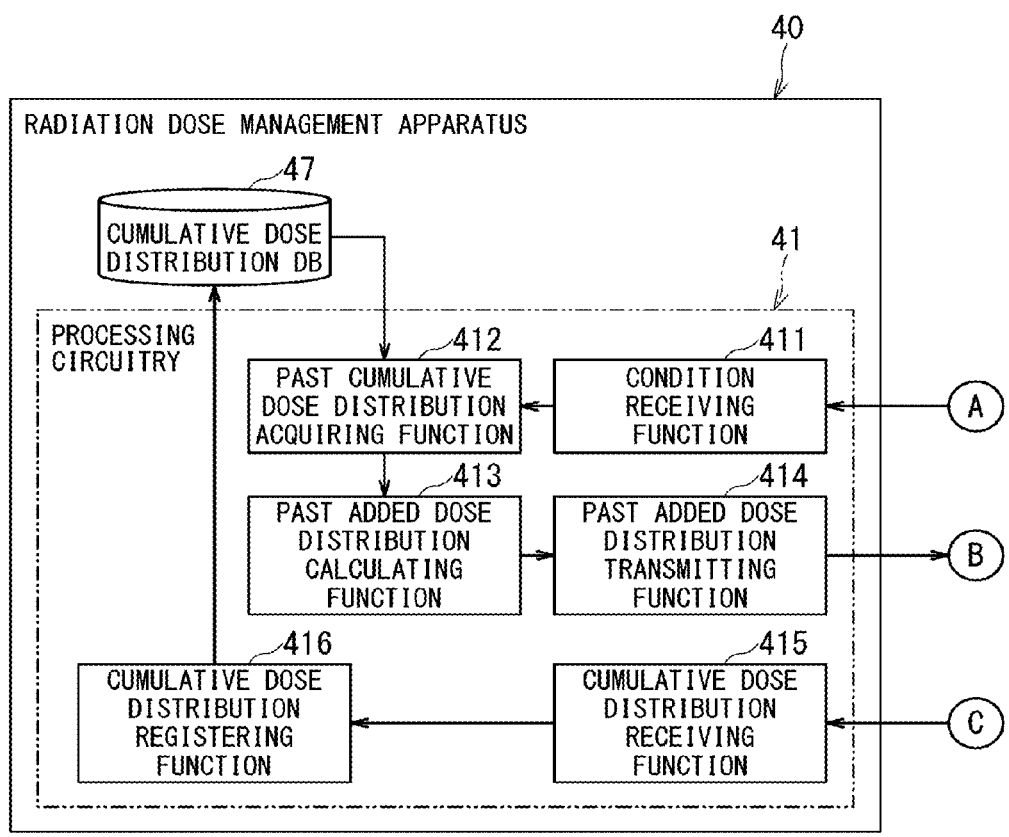
Figure 17B:
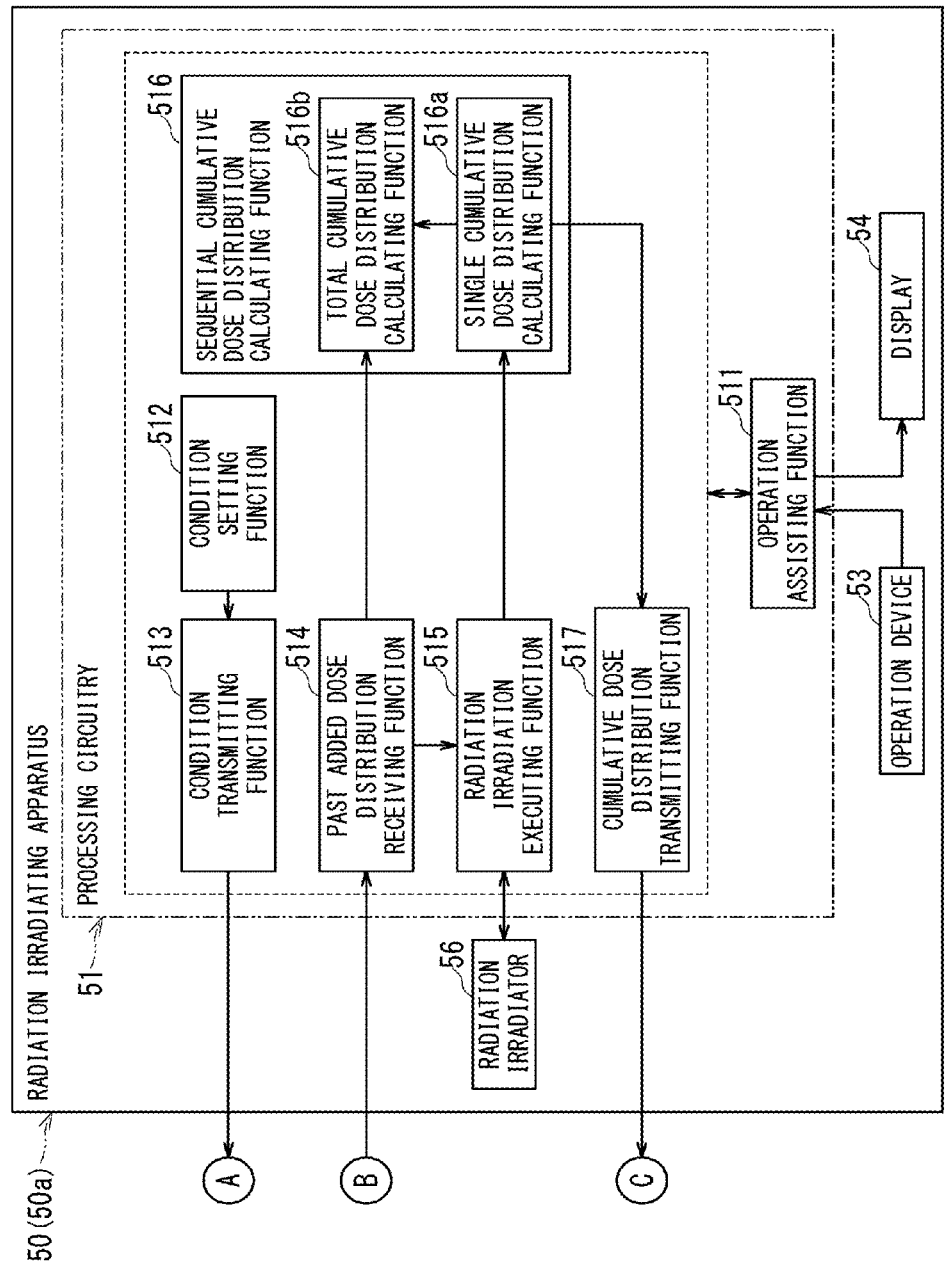
Figure 18A:
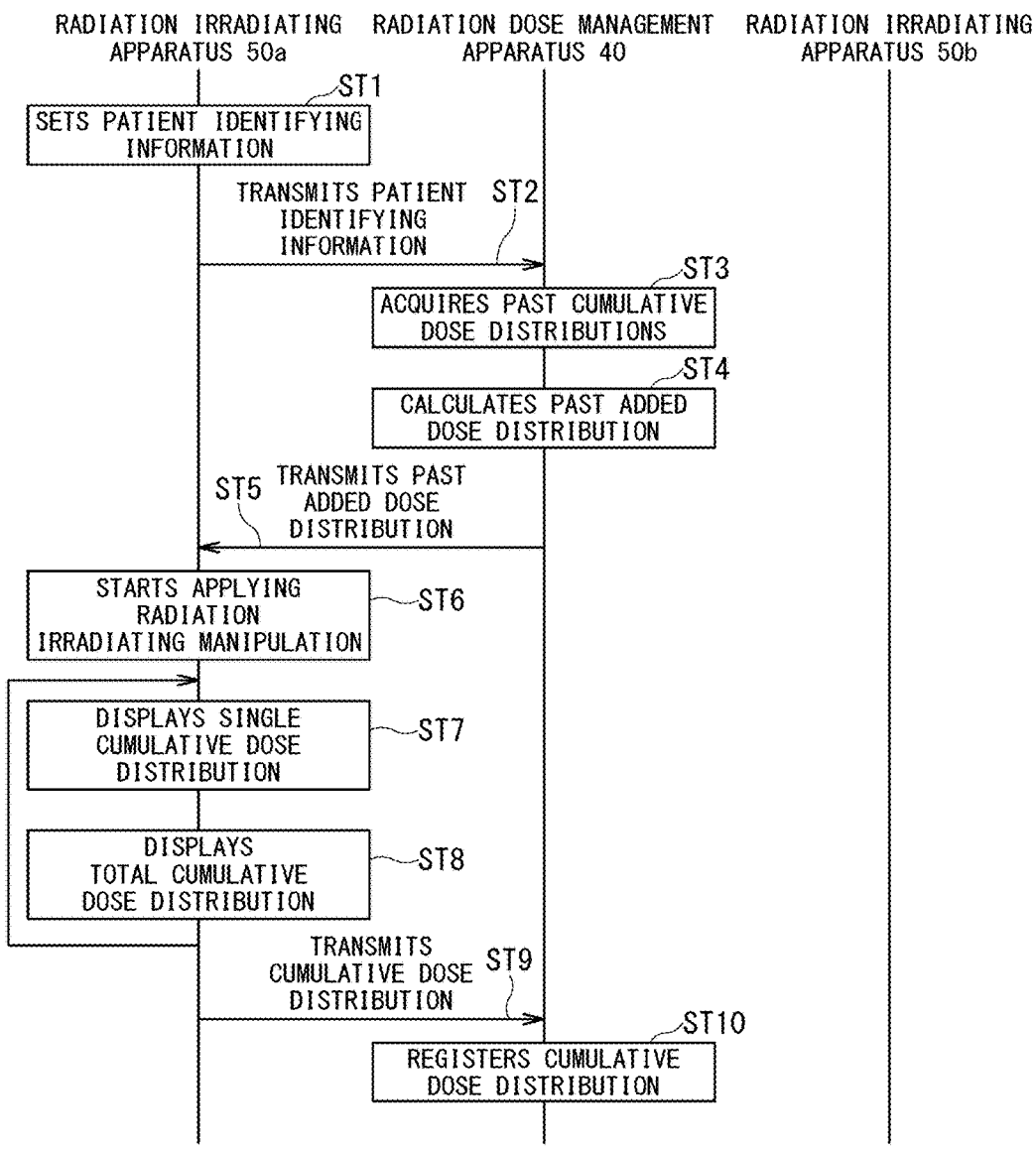
Figure 18B:
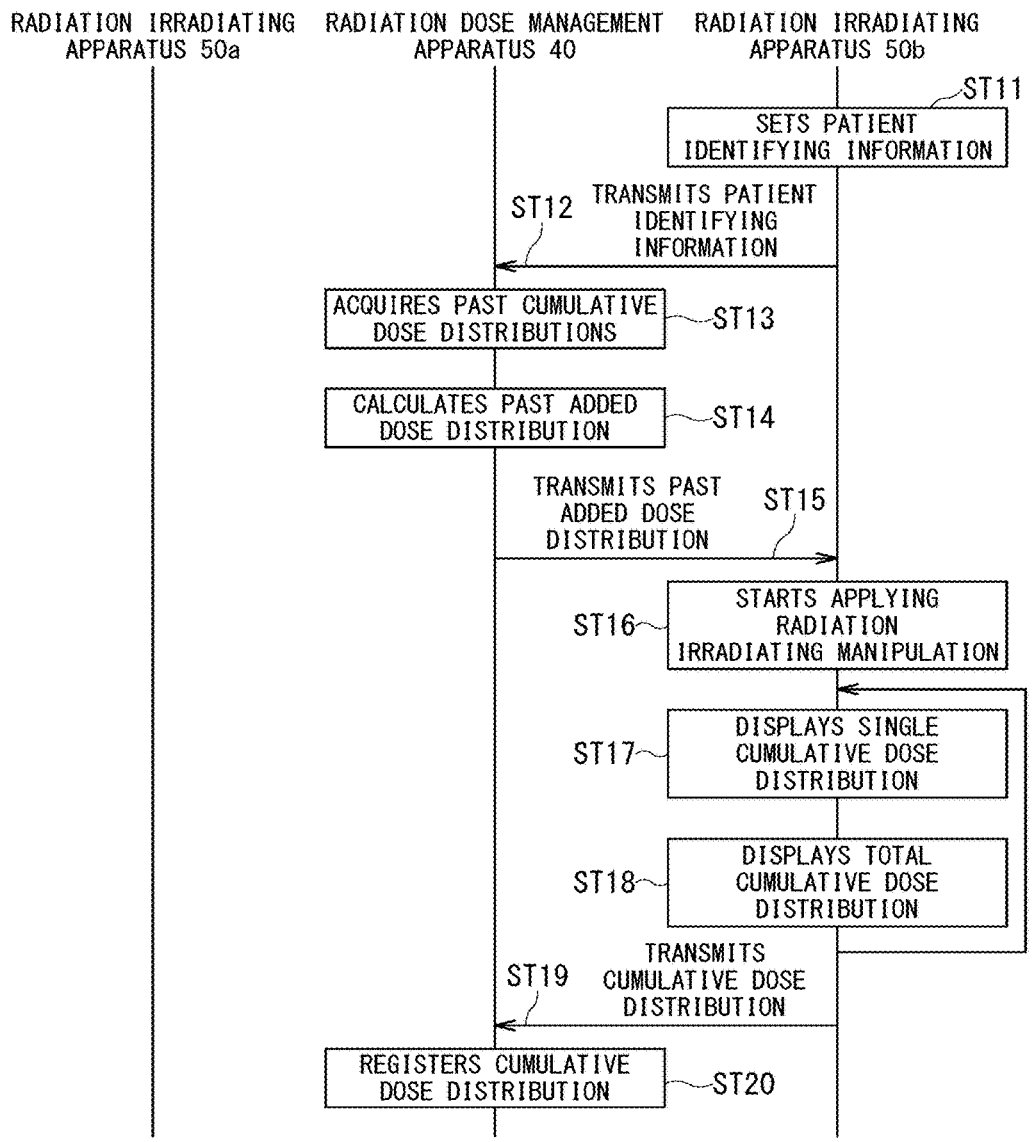

A set of FIGS. 17A and 17B is a block diagram showing functions of the radiation dose management system according to the present embodiment; and A set of FIGS. 18A and 18B is a flowchart showing operations of the radiation dose management system according to the present embodiment.

DETAILED DESCRIPTION

A radiation irradiating apparatus and a radiation dose management system according to a present embodiment are described with reference to the accompanying drawings.

To solve the above-described problems, the present embodiment provides the radiation irradiating apparatus including a processing circuitry configured to: acquire a past cumulative dose distribution associated with patient identifying information, from a storage that is storable a cumulative dose distribution; calculate a first cumulative dose distribution and a second cumulative dose distribution during a radiation irradiation to a patient associated with the patient identifying information, the first cumulative dose distribution being a cumulative dose distribution, the second cumulative dose distribution being generated by adding the first cumulative dose distribution to the past cumulative dose distribution; and display, on a display, at least one of the first and second cumulative dose distributions during the radiation irradiation.

To solve the above-described problems, the present embodiment provides the radiation dose management system including a processing circuitry configured to: acquire a past cumulative dose distribution associated with required patient identifying information, from a storage that is storable a plurality of cumulative dose distributions by a plurality of radiation irradiating apparatuses performing radiation irradiations; calculate a first cumulative dose distribution and a second cumulative dose distribution during a radiation irradiation to a patient associated with the required patient identifying information, the first cumulative dose distribution being a cumulative dose distribution, the second cumulative dose distribution being generated by adding the first cumulative dose distribution to the past cumulative dose distribution; and display, on a display, at least one of the first and second cumulative dose distributions during the radiation irradiation.

(Radiation Irradiating Apparatus)

Figure 1:
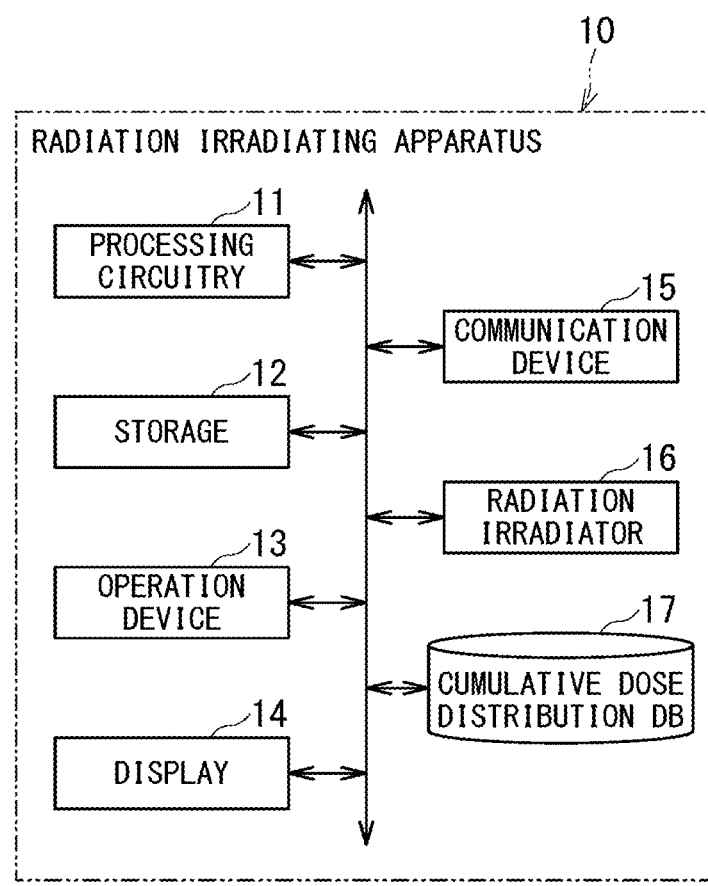
FIG. 1 is a schematic diagram showing a configuration of a radiation irradiating apparatus according to a present embodiment.

FIG. 1 is a schematic diagram showing a configuration of a radiation irradiating apparatus according to a present embodiment.

FIG. 1 shows the radiation irradiating apparatus 10 according to the present embodiment. The radiation irradiating apparatus 10 may be, for example, any of radiation diagnostic apparatuses (radiation exam apparatuses), such as X-ray diagnostic apparatuses (angiography apparatuses, X-ray fluoroscopic imaging apparatuses, etc.) and X-ray computed tomography (CT) apparatuses, and radiation therapeutic apparatuses, such as gamma knives.

The radiation irradiating apparatus 10 has a configuration of a typical computer. The radiation irradiating apparatus 10 roughly includes basic hardware, which is a processing circuitry 11, a storage 12, an operation device 13, a display 14, a communication device 15 and the like, a radiation irradiator 16, and a cumulative dose distribution database (DB) 17. The processing circuitry 11 is mutually connected to each of the hardware configuration elements, which configure the radiation irradiating apparatus 10, via a bus as a common signal transmission path.

The processing circuitry 11 reads various control programs stored in the storage 12 and performs various operations while integrally controlling processing operations in the elements 12 to 17.

The processing circuitry 11 means any one of dedicated or general central processing unit (CPU) and a micro processor unit (MPU), an application specific integrated circuit (ASIC), and a programmable logic device. The programmable logic device may be, for example, any one of a simple programmable logic device (SPLD), a complex programmable logic device (CPLD), a field programmable gate array (FPGA) and the like. The processing circuitry 11 reads programs stored in the storage 12 or directly implemented in the processing circuitry 11 and executes these programs to thereby achieve functions 111 to 117 shown in FIG. 5.

The processing circuitry 11 may be a single circuit or a combination of separate circuits. In the latter case, the storage 12, which stores the programs, may be separately provided for each of the circuits. Alternatively, a single storage 12 may store the programs corresponding to the functions of the multiple circuits.

The storage 12 includes a memory and a hard disc drive (HDD). The storage 12 stores data required to execute the control programs used in the processing circuitry 11, and various types of data.

The operation device 13 includes a keyboard and a mouse. When an operator operates the operation device 13, this unit 13 generates an operation signal corresponding to the operation, and outputs the operation signal to the processing circuitry 11. Alternatively, a touch panel that integrally includes this operation device 13 and the display 14 may be provided.

The display 14 includes a display unit, such as a liquid crystal display (LCD). The display 14 displays various operation screens on the display unit according to instructions from the processing circuitry 11.

The communication device 15 includes a connector in conformity with a parallel connection specification or a serial connection specification. The communication device 15 transmits and receives information to and from external apparatuses on networks.

The radiation irradiator 16 includes a structure (not shown) for emitting radiation. The radiation irradiator 16 is a device that irradiates a patient with radiation under control of the processing circuitry 11. In the case where the radiation irradiating apparatus 10 is an X-ray diagnostic apparatus, the radiation irradiator 16 includes typical structures, such as a high voltage generator, an X-ray source (X-ray tube), an X-ray detector, a C-arm, and a bed. In the case where the radiation irradiating apparatus 10 is an X-ray CT apparatus, the radiation irradiator 16 includes typical structures, such as a high voltage generator, an X-ray source, an X-ray detector, a rotation unit, and a bed. In the case where the radiation irradiating apparatus 10 is a radiation therapeutic apparatus, the radiation irradiator 16 includes typical structures, such as a high voltage generator, a radiation source, a rotation unit, and a bed.

Figure 2:
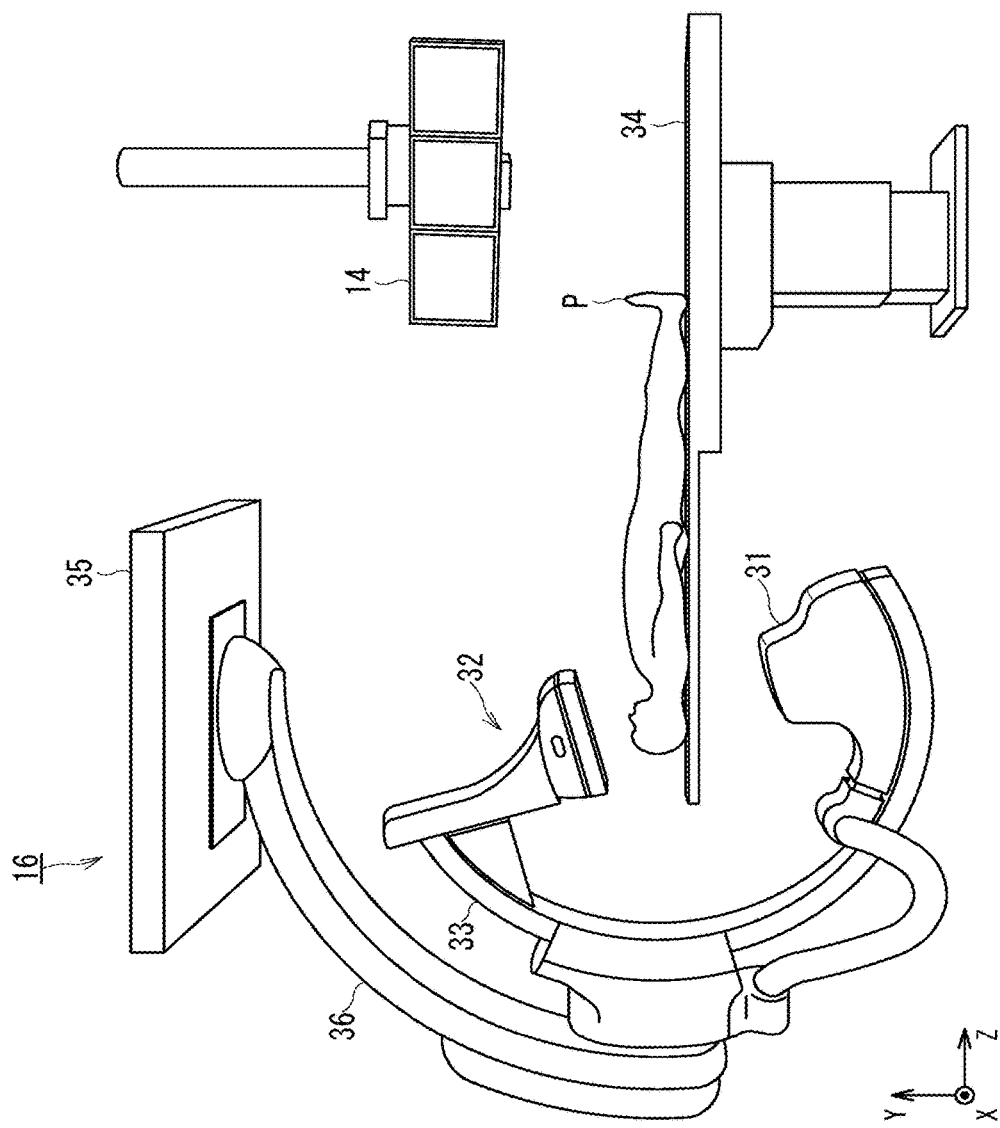
FIG. 2 is a diagram showing a configuration example of a part of a radiation irradiator in the case where the radiation irradiating apparatus is an X-ray diagnostic apparatus.

FIG. 2 is a diagram showing a configuration example of a part of the radiation irradiator in the case where the radiation irradiating apparatus 10 is an X-ray diagnostic apparatus.

FIG. 2 shows a part of the radiation irradiator 16 and the display 14. The radiation irradiator 16 includes an X-ray tube 31, an X-ray detector 32, a C-arm 33, and a table-top 34.

The X-ray tube 31 generates X-rays through application of a high voltage (tube voltage) by a high voltage generator, not shown. The X-ray tube 31 is attached to one end of the C-arm 33. The X-ray detector 32 is attached to the other end of the C-arm 33 opposite to the X-ray tube 31. The example is herein described where the radiation irradiator 16 includes the C-arm 33, and this C-arm 33 causes the X-ray tube 31 and the X-ray detector 32 to integrally operate. However, the technique is not limited to this case. For example, a configuration may be adopted where the radiation irradiator 16 does not include C-arm 33 and causes the X-ray tube 31 and the X-ray detector 32 to operate separately from each other instead.

The X-ray detector 32 is a flat panel detector that includes two-dimensionally arranged detection elements (pixels) for directly or indirectly converting incident X-rays into electric charges. However, the X-ray detector 32 may include an image intensifier (I. I.) and a TV camera. During imaging through X-ray irradiation, an object (patient) P is arranged between the X-ray tube 31 and the X-ray detector 32 in a state of being mounted on the table-top 34.

The C-arm 33 is supported by a ceiling base 35 via a suspension arm 36 so as to be rotatable under a predetermined limitation with respect to each of X, Y and Z directions, which are orthogonal to each other, in order to freely change the angle at which the patient P is irradiated with X-rays. The line passing from the X-ray focal point of the X-ray tube 31 to the center of detection plane of the X-ray detector 32 is referred to as an imaging axis. The imaging angle is typically defined as the angles at which the imaging axis intersects with the respective X, Y and Z directions. According to convention, the angles are represented as a first oblique position (RAO: right anterior oblique position), second oblique position (LAO: left anterior oblique position), third oblique position (LPO: left posterior oblique position) and fourth oblique position (RPO: right posterior oblique position). Typically, the Z direction is defined to coincide with the longitudinal direction of the table-top 34.

Returning to the description with respect to FIG. 1, the cumulative dose distribution DB 17 is a storage that includes an HDD and a memory. The cumulative dose distribution DB 17 can store data on the cumulative dose distribution that represents the distribution of three-dimensional cumulative dose (mGy) accompanied by patient identifying information (patient ID) for identifying a patient and by execution time information on past radiation irradiating manipulations (examinations (imaging), therapy and surgery through radiation irradiation). The cumulative dose distribution is typically generated with respect to each radiation irradiating manipulation.

Figure 3:
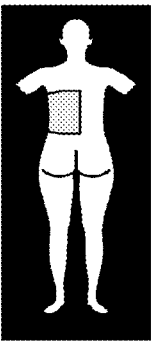
FIG. 3 is a diagram showing an example of data on a cumulative dose distribution.
Figure 3:
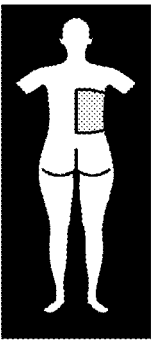
Figure 3:
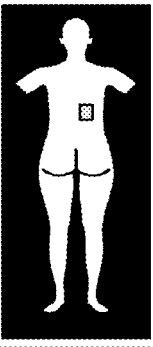
Figure 3:
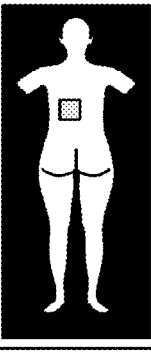

FIG. 3 is a diagram showing an example of data on the cumulative dose distribution.

As shown in FIG. 3, the cumulative dose distribution DB (shown in FIG. 1) can store multiple cumulative dose distributions where cumulative doses in a model coordinate system are associated with respective body surface positions of a three-dimensional human body model. Each cumulative dose distribution is accompanied by the patient identifying information contained in patient information and the execution time information.

FIG. 3 shows the case where mapping of the cumulative doses to the body surface positions of the human body model is stored as the cumulative dose distribution. Alternatively, data on the human body model, and the cumulative doses on the body surface positions may be separately stored. Instead of the human body model, volume data that has already been generated and encompasses the entire patient may be used.

Figure 4:
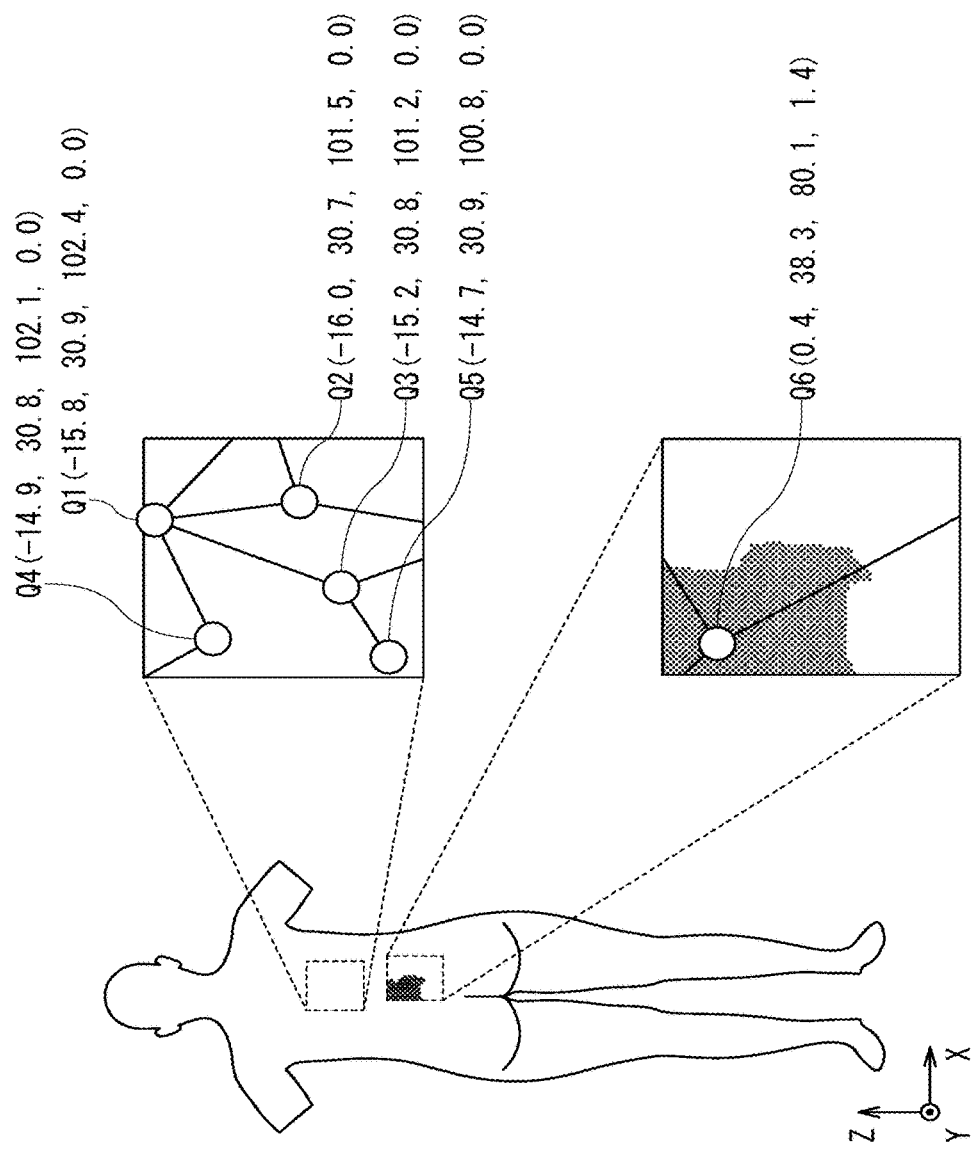
FIG. 4 is a diagram for showing details of the data on the cumulative dose distribution.

FIG. 4 is a diagram for showing details of the data on the cumulative dose distribution.

As shown in FIG. 4, the cumulative dose distribution in the human body model coordinate system is based on the cumulative doses on the body surface positions (points) Q1 to Q6 in the human body model. The body surface positions Q1 to Q6 are associated with information on the X coordinate, Y coordinate, Z coordinate, and cumulative dose (mGy). Here, the X coordinate corresponds to the lateral direction of the patient. The Y coordinate corresponds to the ventrodorsad direction of the patient. The Z coordinate corresponds to the body axis direction of the patient. The cumulative doses on the body surface positions may be registered separately from or together with the human body model. In the case with no exposure dose (body surface positions Q1 to Q6), the cumulative dose is 0 mGy.

Figure 5:
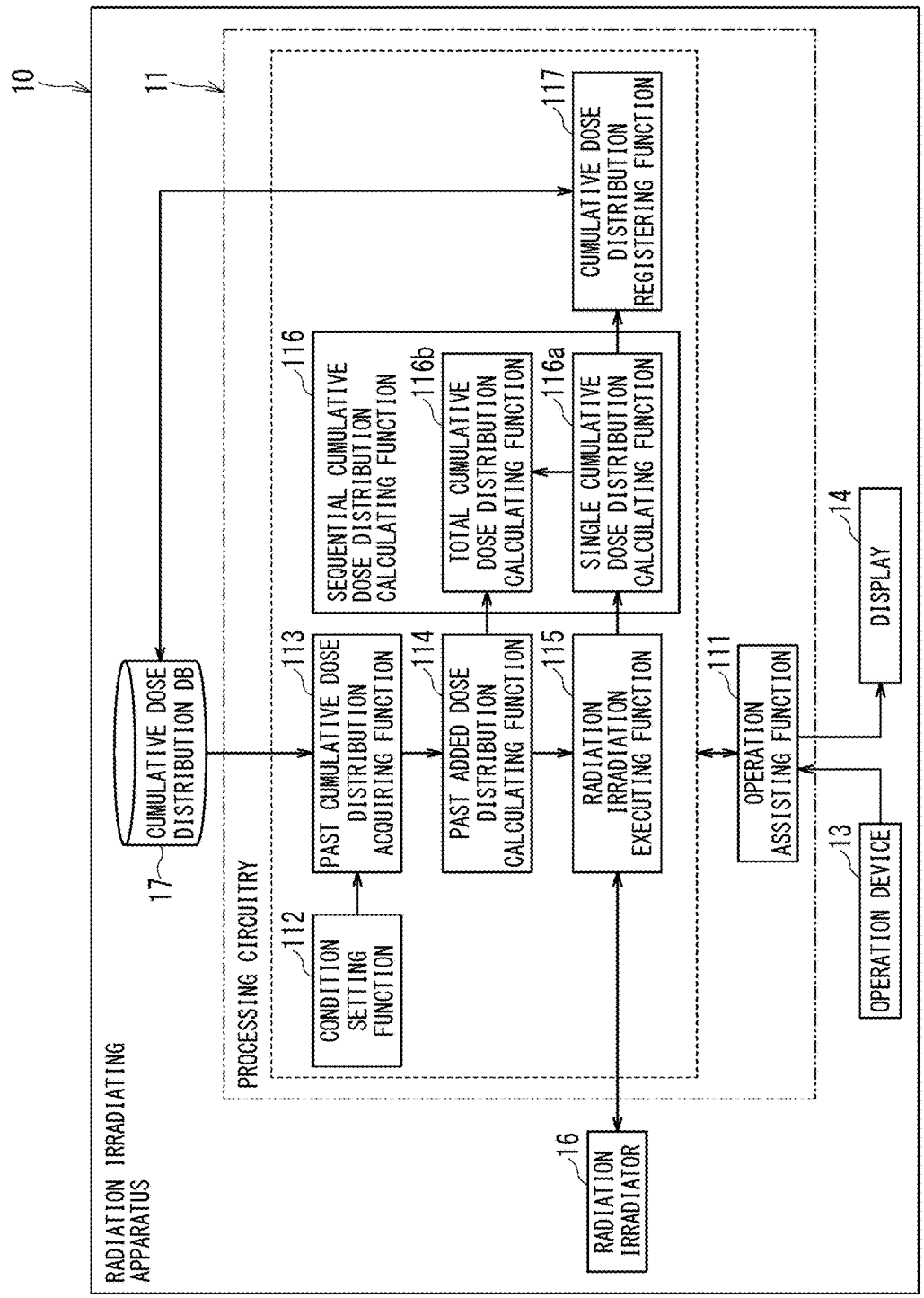
FIG. 5 is a block diagram showing functions of the radiation irradiating apparatus according to the present embodiment.

FIG. 5 is a block diagram showing functions of the radiation irradiating apparatus 10 according to the present embodiment.

The processing circuitry 11 included in the radiation irradiating apparatus 10 according to the present embodiment executes the programs to thereby cause the radiation irradiating apparatus 10 to function as an operation assisting function 111, a condition setting function 112, a past cumulative dose distribution acquiring function 113, a past added dose distribution calculating function 114, a radiation irradiation executing function 115, a sequential cumulative dose distribution calculating function 116, and a cumulative dose distribution registering function 117. The description is made assuming that the functions 111 to 117 function as software. Alternatively, all or some of the functions 111 to 117 may be implemented as hardware in the radiation irradiating apparatus 10.

The operation assisting function 111 is an interface between the functions 112 to 117 and the operation device 13 and display 14, and may be a graphical user interface (GUI) or the like.

The condition setting function 112 sets the patient identifying information (patient ID) based on an operation at the operation device 13 through the operation assisting function 111. The patient ID is used for acquiring the past cumulative dose distributions pertaining to the patient subjected to the radiation irradiating manipulation. Furthermore, the condition setting function 112 may set a period condition for acquiring only the cumulative dose distributions in a specific period among all the past cumulative dose distributions pertaining to the patient subjected to the radiation irradiating manipulation.

The past cumulative dose distribution acquiring function 113 acquires (reads), from the cumulative dose distribution DB 17, the past cumulative dose distributions associated with the patient identifying information set by the condition setting function 112. When the condition setting function 112 sets the period condition, the past cumulative dose distribution acquiring function 113 acquires, from the cumulative dose distribution DB 17, the cumulative dose distributions associated with the patient identifying information set by the condition setting function 112 and with the execution time information within the range of the period condition.

For example, if patient identifying information "P1" is set by the condition setting function 112, the past cumulative dose distribution acquiring function 113 acquires three past cumulative dose distributions associated with the patient identifying information "P1" from among the past cumulative dose distributions shown in FIG. 3. If the patient identifying information "P1" and a period condition "2013/01/01 to Present" are set by the condition setting function 112, the past cumulative dose distribution acquiring function 113 acquires two past cumulative dose distributions that are associated with the patient identifying information "P1" and are within the range of the period condition "2013/01/01 to Present" from among the past cumulative dose distributions shown in FIG. 3.

The past added dose distribution calculating function 114 aligns, when the past cumulative dose distributions are acquired by the past cumulative dose distribution acquiring function 113, the past cumulative dose distributions, and adds (or totalizes) the distributions with respect to the body surface positions of the human body model, thereby calculating the data on a past added dose distribution pertaining to the past radiation irradiating manipulations.

That is, when the past cumulative dose distributions are acquired by the past cumulative dose distribution acquiring function 113, the past added dose distribution calculating function 114 adds the past cumulative doses with respect to the body surface positions, thereby calculating the data on the past added dose distribution pertaining to the past radiation irradiating manipulations. In the case where one past cumulative dose distribution is acquired by the past cumulative dose distribution acquiring function 113, the past added dose distribution calculating function 114 is unnecessary.

Figure 6:
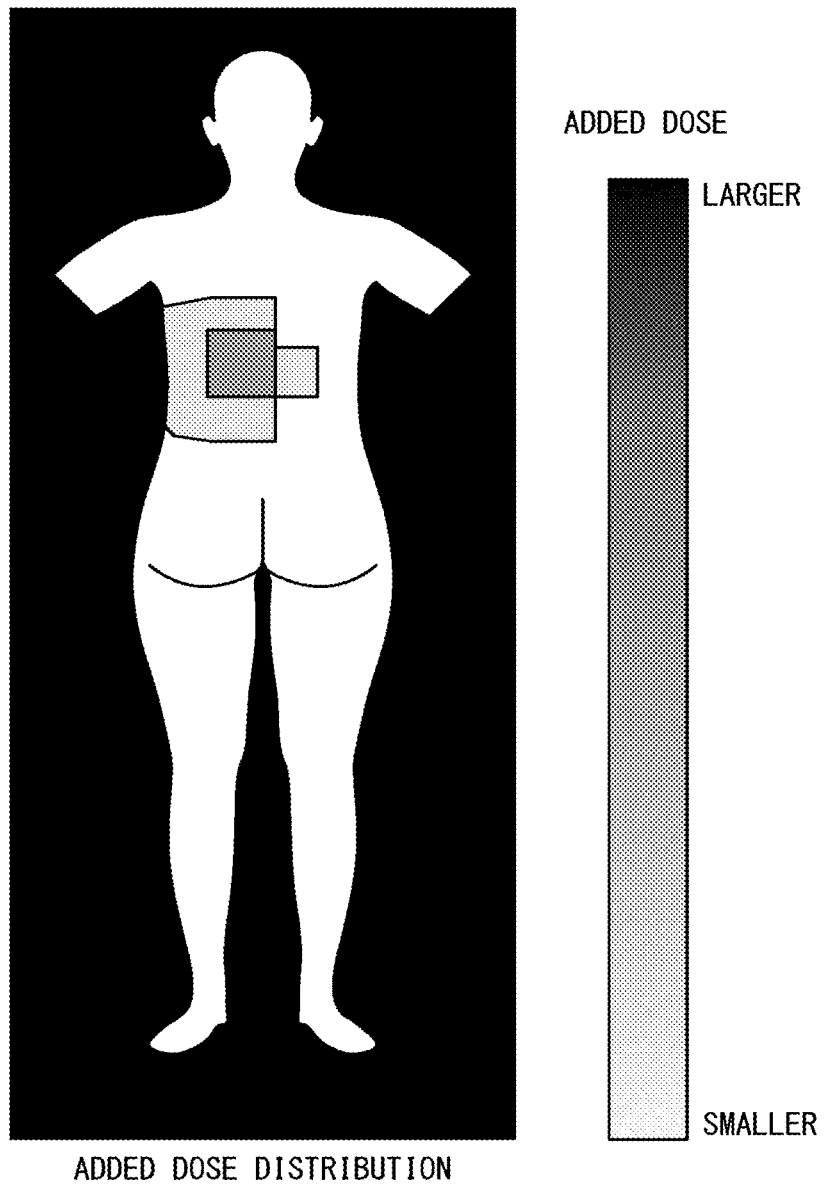
FIG. 6 is a diagram showing an example of data on a past added dose distribution.

FIG. 6 is a diagram showing an example of data on the past added dose distribution.

FIG. 6 shows the past added dose distribution. The past cumulative dose distributions are aligned and added to acquire the past added dose distribution. For example, FIG. 6 shows the distribution acquired by aligning and adding three cumulative dose distributions associated with the patient identifying information "P1 " shown in FIG. 3.

Returning to the description with reference to FIG. 5, when the past added dose distribution calculating function 114 aligns and adds the past cumulative dose distributions acquired by the cumulative dose distribution acquiring function 113, the function 114 may perform weighted addition by multiplying the cumulative dose distributions by respective coefficients (of a linear function, an exponential function, a logarithmic function, a combination thereof, etc.). The coefficients are set so as to attach importance to radiation irradiation from which shorter time has elapsed than radiation irradiation from which longer time has elapsed. In the case of therapeutic radiation irradiation, the coefficients are set so as to consider the recovering degree of cells having been irradiated with radiation.

The radiation irradiation executing function 115 applies a radiation irradiating manipulation to the patient associated with the patient identifying information set by the condition setting function 112. Here, in the case where the radiation irradiating apparatus 10 is an X-ray diagnostic apparatus or an X-ray CT apparatus, the radiation irradiation executing function 115 controls the operation of the radiation irradiator 16 to collect an image pertaining to the detection portion of the patient while emitting radiation. When the radiation irradiating apparatus 10 is the X-ray diagnostic apparatus, the radiation irradiation executing function 115 sequentially generates each of fluoroscopic images based on the X-rays having passed through the patient, and displays the fluoroscopic images as a moving image. In the case where the radiation irradiating apparatus 10 is a radiation therapeutic apparatus, the radiation irradiation executing function 115 controls the operation of the radiation irradiator 16 to irradiate a therapy target portion of the patient.

The sequential cumulative dose distribution calculating function 116 cumulates, during execution of the radiation irradiating manipulation by the radiation irradiation executing function 115, the exposure doses until the present time, thereby calculating the cumulative dose. The sequential cumulative dose distribution calculating function 116 calculates the cumulative dose distribution that associates the cumulative doses with the body surface positions of the human body model.

The sequential cumulative dose distribution calculating function 116 can sequentially (e.g. in real time) calculate, during execution of the radiation irradiating manipulation, the cumulative dose and the cumulative dose distribution. Alternatively, at any timing in execution of the radiation irradiating manipulation, the sequential cumulative dose distribution calculating function 116 can calculate the cumulative dose and the cumulative dose distribution. Any timing means, for example, a timing designated by the operator. The case is hereinafter described where the sequential cumulative dose distribution calculating function 116 sequentially calculates the cumulative dose and the cumulative dose distribution during execution of the radiation irradiating manipulation.

The body surface position of the patient in the real coordinate system is coordinate-transformed into the corresponding body surface position in the human body model in the model coordinate system. This transformation allows the cumulative dose pertaining to the body surface position of the patient in the real coordinate system to be considered as the cumulative dose on the corresponding body surface position of the human body model. The sequential cumulative dose distribution calculating function 116 includes a single cumulative dose distribution calculating function 116a, and a total cumulative dose distribution calculating function 116b.

The single cumulative dose distribution calculating function 116a sequentially calculates, as the single cumulative dose distribution, the cumulative dose distribution from the start of the radiation irradiating manipulation under execution to the present time during execution of the radiation irradiating manipulation. The single cumulative dose distribution associates the cumulative doses from the start of the radiation irradiating manipulation under execution to the present time with the body surface positions of the human body model.

The total cumulative dose distribution calculating function 116b sequentially adds the single cumulative dose distribution calculated by the single cumulative dose distribution calculating function 116a to the past added dose distribution calculated by the past added dose distribution calculating function 114, during execution of the radiation irradiating manipulation. The total cumulative dose distribution calculating function 116b calculates the total cumulative dose distribution to the present time from the start of the radiation irradiating manipulation pertaining to the latest cumulative dose distribution among the past cumulative dose distributions. The total cumulative dose distribution associates, with the body surface positions of the human body model, the total cumulative doses to the present time from the start of the radiation irradiating manipulation pertaining to the latest cumulative dose distribution among the past cumulative dose distributions.

When the one past cumulative dose distribution is acquired by the past cumulative dose distribution acquiring function 113, the total cumulative dose distribution calculating function 116b sequentially adds the single cumulative dose distribution calculated by the single cumulative dose distribution calculating function 116a to one past cumulative dose distribution acquired by the past cumulative dose distribution acquiring function 113, during execution of the radiation irradiating manipulation. The total cumulative dose distribution calculating function 116b calculates the total cumulative dose distribution to the present time from the start of the radiation irradiating manipulation pertaining to the one past cumulative dose distribution.

The sequential cumulative dose distribution calculating function 116 displays, on the display 14, the single cumulative dose distribution and the total cumulative dose distribution through the operation assisting function 111 during execution of the radiation irradiating manipulation. That is, the sequential cumulative dose distribution calculating function 116 displays, on the display 14, the single cumulative dose distribution at a timing in execution of the radiation irradiating manipulation while displaying, on the display 14, the total cumulative dose distribution at a timing in execution of the radiation irradiating manipulation. The sequential cumulative dose distribution calculating function 116 sequentially displays both of the single cumulative dose distribution and the total cumulative dose distribution during execution of the radiation irradiating manipulation (FIGS. 8 and 10 to 14), or switches between sequential display of the single cumulative dose distribution and the sequential display of the total cumulative dose distribution (FIG. 9). That is, the sequential cumulative dose distribution calculating function 116 sequentially calculates a distribution to be displayed that is at least one of the single cumulative dose distribution and the total cumulative dose distribution, and sequentially displays the distribution, during execution of the radiation irradiating manipulation.

The sequential cumulative dose distribution calculating function 116 is able to sequentially display, on the display 14, the distribution to be displayed, and display, on the display 14, the fluoroscopic images as a moving image, the fluoroscopic images being generated by the X-ray diagnostic apparatus as the radiation irradiating apparatus 10.

Thus, the sequential cumulative dose distribution calculating function 116 sequentially calculates both of the single cumulative dose distribution and the total cumulative dose distribution, thereby allowing both of the single cumulative dose distribution and the total cumulative dose distribution to be displayed in a juxtaposed manner. The sequential cumulative dose distribution calculating function 116 sequentially calculates both of the single cumulative dose distribution and the total cumulative dose distribution, thereby allowing one of the distributions to be sequentially displayed in a switchable manner while allowing the other distribution to be displayed immediately after switching to the other distribution.

Figure 7:
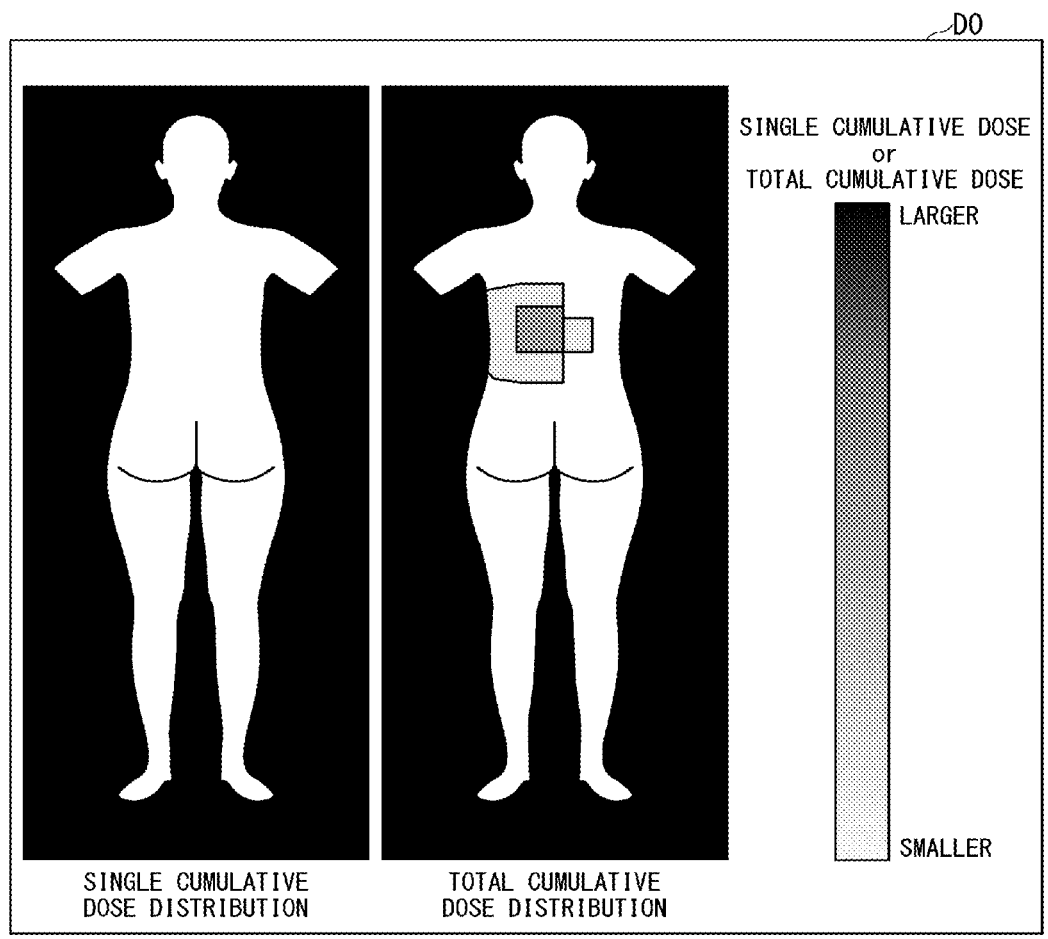
FIG. 7 is a diagram showing a display screen of a single cumulative dose distribution and a total cumulative dose distribution in an initial state.

FIG. 7 is a diagram showing a display screen of the single cumulative dose distribution and the total cumulative dose distribution in an initial state.

A display screen DO shown in FIG. 7 contains the single cumulative dose distribution and the total cumulative dose distribution before start of the radiation irradiating manipulation by the radiation irradiation executing function 115 (shown in FIG. 5) (in the initial state). The radiation irradiating manipulation by the radiation irradiation executing function 115 has not been started yet. Accordingly, the single cumulative dose distribution is only of the human body model. The total cumulative dose distribution is the past added dose distribution in consideration of the human body model. The total cumulative dose distribution is provided with color attribute information (including at least one of hue information, lightness information, and chroma saturation information) according to the degree of the total cumulative dose for each body surface position of the human body model.

The single cumulative dose distribution and the total cumulative dose distribution in the initial state are each three-dimensional data. Consequently, when the distributions are displayed on the display screen DO, the distributions are displayed as three-dimensional images having been subjected to a rendering process based on a freely selected viewpoint. The freely selected viewpoint can be appropriately changed.

Figure 8:
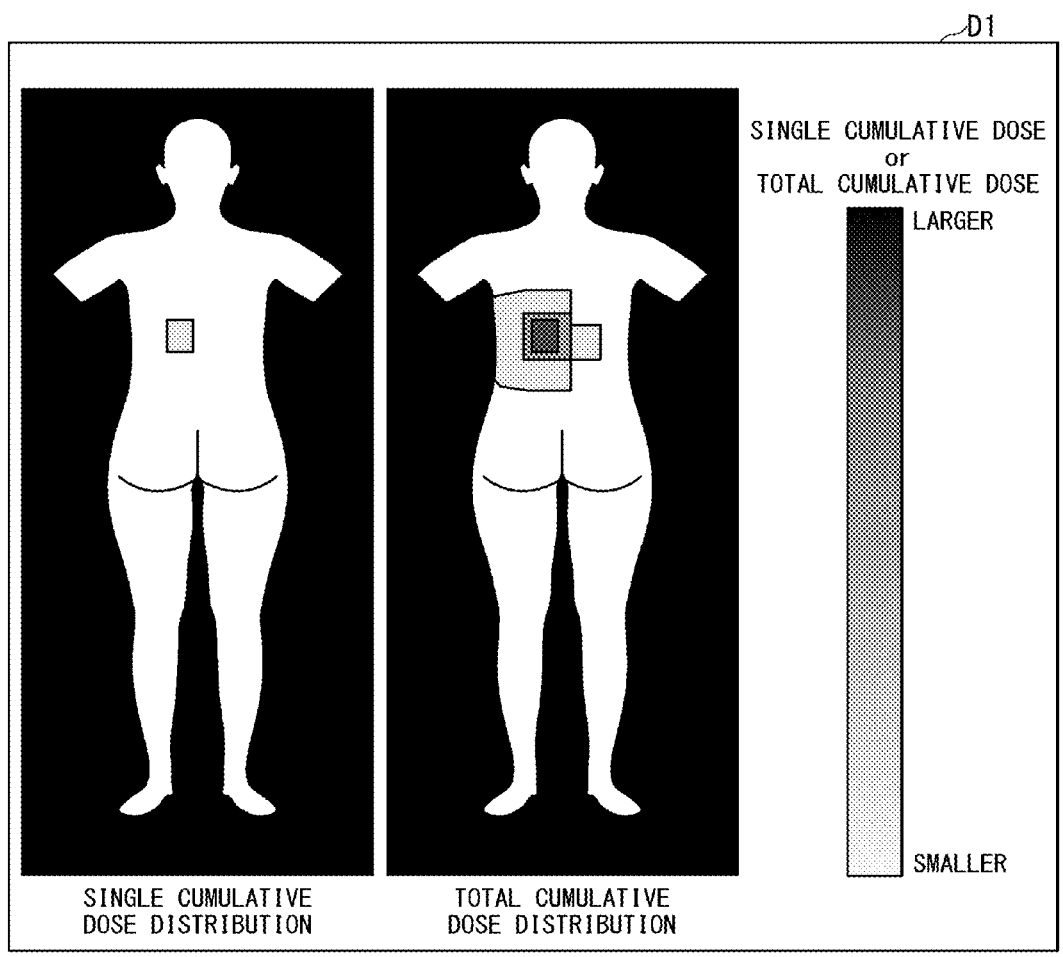
FIG. 8 is a diagram showing a first display screen of the single cumulative dose distribution and the total cumulative dose distribution that are sequentially calculated during a radiation irradiating manipulation under execution.
Figure 9:
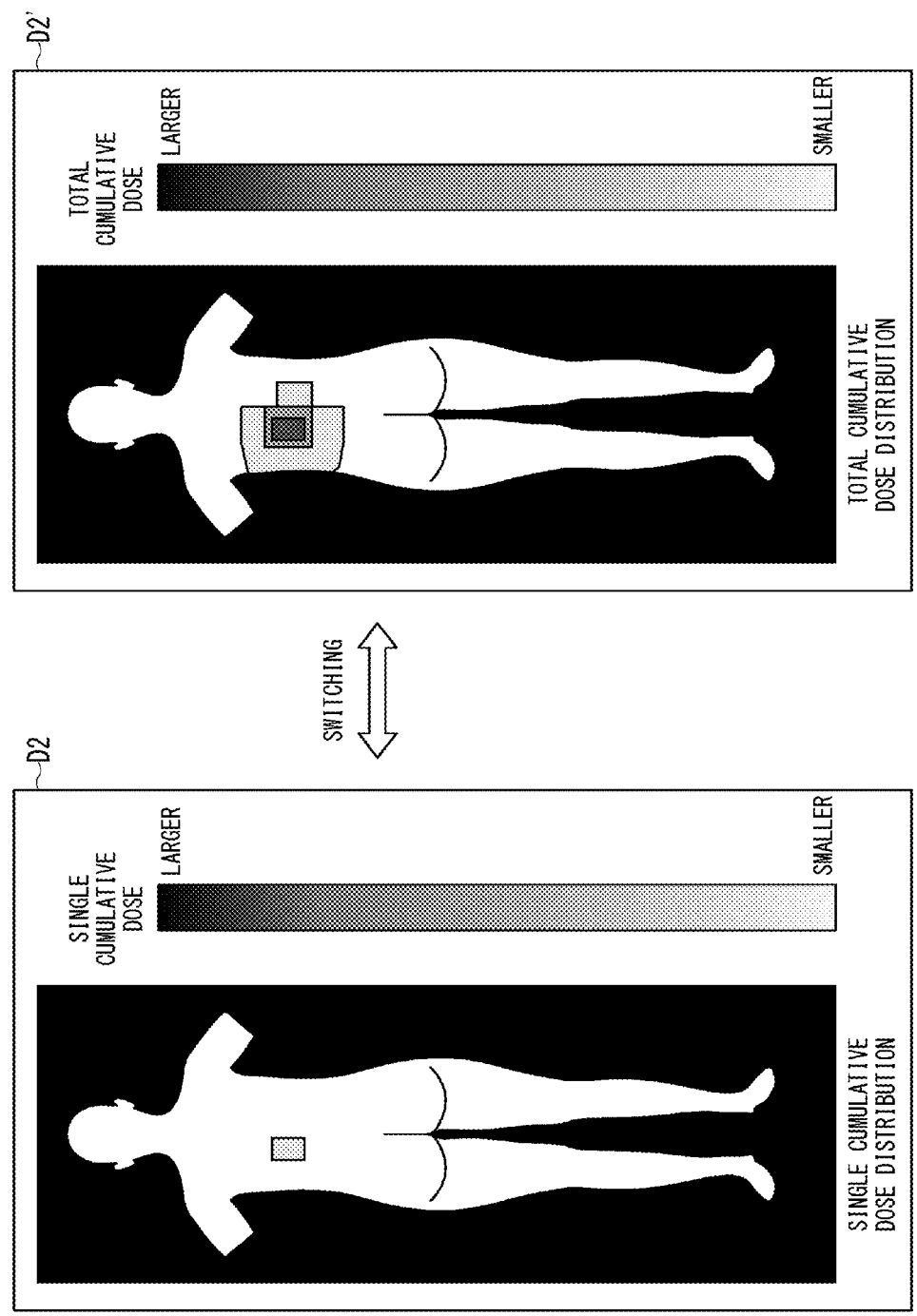
FIG. 9 is a diagram showing a second display screen of the single cumulative dose distribution and the total cumulative dose distribution that are sequentially calculated during a radiation irradiating manipulation under execution.

The display screen shown in FIG. 7 is an initial screen of a first display screen shown in FIG. 8. The initial screen of second to sixth display screens shown in FIGS. 9 to 14 is the same.

FIG. 8 is a diagram showing a first display screen (screen displayed in a juxtaposed manner) of the single cumulative dose distribution and the total cumulative dose distribution that are sequentially calculated during the radiation irradiating manipulation under execution.

A display screen D1 shown in FIG. 8 contains the single cumulative dose distribution and the total cumulative dose distribution that are sequentially displayed in a juxtaposed manner. The single cumulative dose distribution on the display screen D1 is sequentially updated. The update allows the operator to sequentially view the cumulative dose from the start of the radiation irradiating manipulation under execution to the present time. The total cumulative dose distribution on the display screen D1 is sequentially updated. The update allows the operator to sequentially view the cumulative dose to the present time from the past radiation irradiating manipulations pertaining to the patient.

FIG. 9 is a diagram showing a second display screen (screen displayed in a switchable manner) of the single cumulative dose distribution and the total cumulative dose distribution that are sequentially calculated during the radiation irradiating manipulation under execution.

The display screen shown in FIG. 9 switches between a display screen D2 for sequentially displaying the single cumulative dose distribution and a display screen D2' for sequentially displaying the total cumulative dose distribution. The single cumulative dose distribution on the display screen D2 is sequentially updated while the display screen D2 is displayed. The update allows the operator to sequentially view the cumulative dose from the start of the radiation irradiating manipulation under execution to the present time. The total cumulative dose distribution on the display screen D2' is sequentially updated while the display screen D2' is displayed. The update allows the operator to sequentially view the cumulative dose to the present time from the past radiation irradiating manipulations pertaining to the patient.

The display of the cumulative dose distribution is switched from the display screen D2 to the display screen D2' and from the display screen D2' to the display screen D2 at a required timing. The switching timing may be according to an operation through the operation device 13 (shown in FIG. 5), or be a timing when the cumulative dose reaches a threshold (a timing of an alarm sound). Alternatively, the switching timing may be according to a preset time interval.

Figure 10:
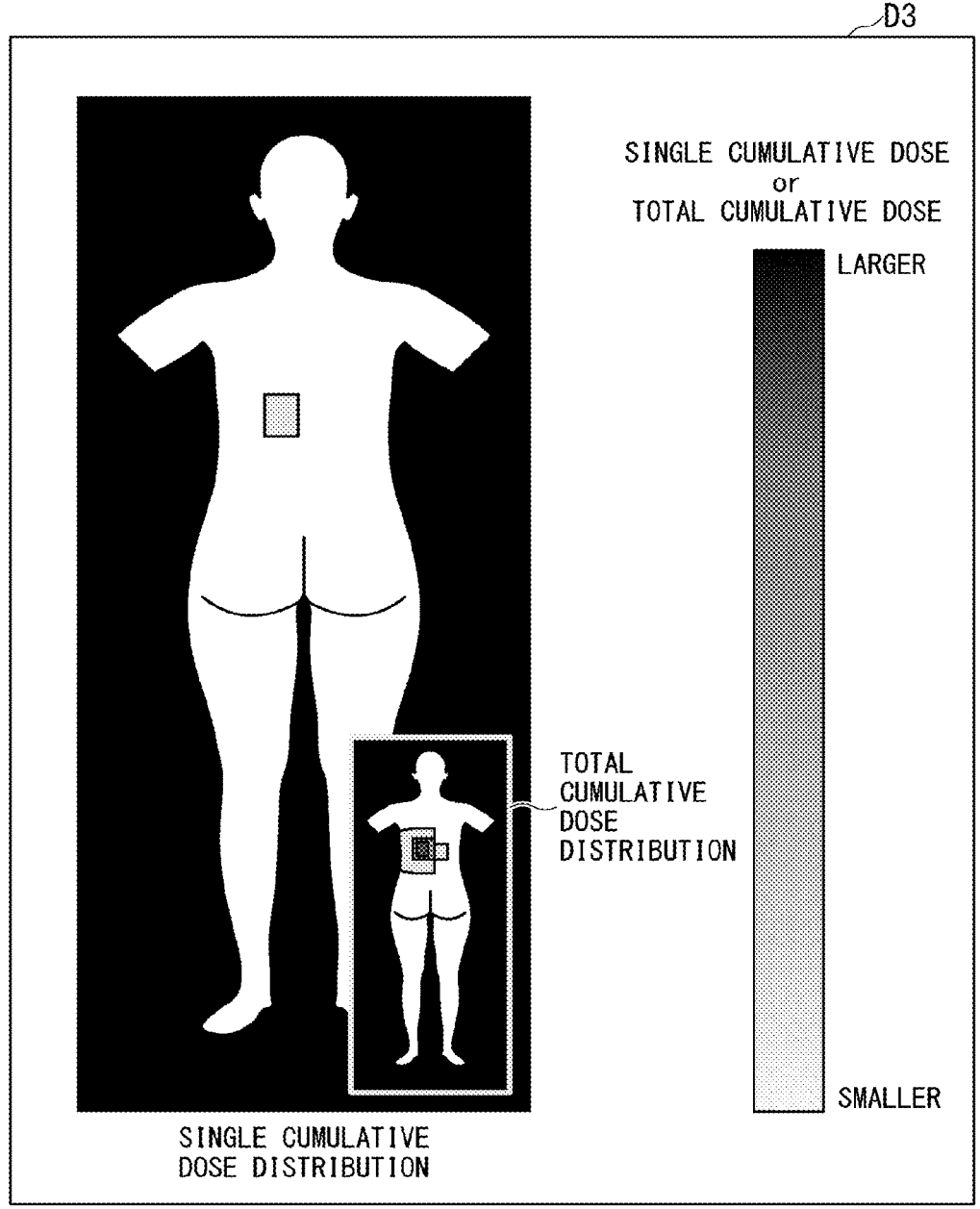
FIG. 10 is a diagram showing a third display screen of the single cumulative dose distribution and the total cumulative dose distribution that are sequentially calculated during a radiation irradiating manipulation under execution.

FIG. 10 is a diagram showing a third display screen (zoom-in-and-out display screen) of the single cumulative dose distribution and the total cumulative dose distribution that are sequentially calculated during the radiation irradiating manipulation under execution.

A display screen D3 shown in FIG. 10 contains the single cumulative dose distribution and the total cumulative dose distribution, one of which is zoomed in and sequentially displayed, and the other of which is zoomed out and sequentially displayed. For example, on the display screen D3, the single cumulative dose distribution is zoomed in and displayed while the total cumulative dose distribution is zoomed out and displayed. The single cumulative dose distribution on the display screen D3 is sequentially updated. The update allows the operator to sequentially view the cumulative dose from the start of the radiation irradiating manipulation under execution to the present time. The total cumulative dose distribution on the display screen D3 is sequentially updated. The update allows the operator to sequentially view the cumulative dose to the present time from the past radiation irradiating manipulations pertaining to the patient.

On the display screen D3 shown in FIG. 10, the single cumulative dose distribution is zoomed in and displayed while the total cumulative dose distribution is zoomed out and displayed. Alternatively, the object to be zoomed in and displayed and the object to be zoomed out and displayed may be replaced with each other. A configuration may be adopted that can freely switch between the zoom-in display and the zoom-out display.

Figure 11:
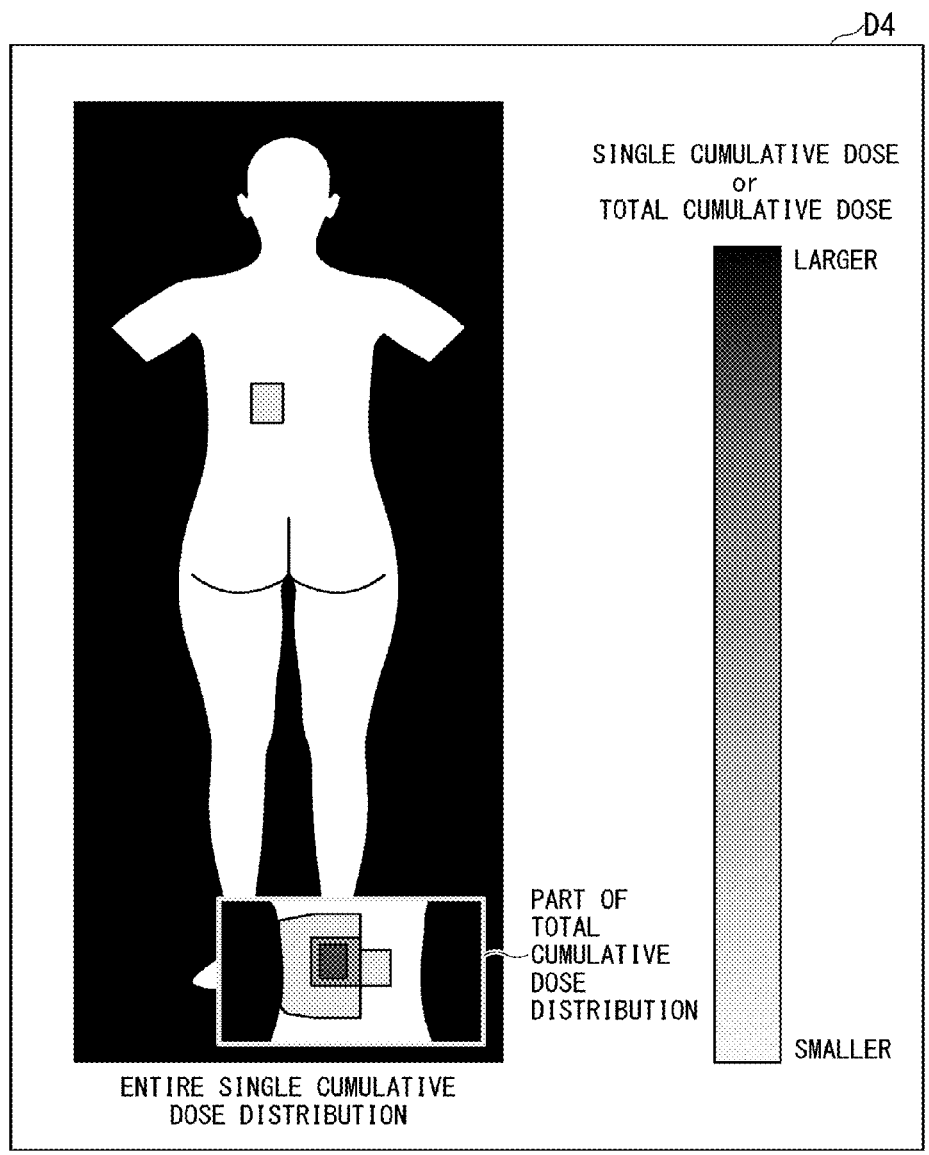
FIG. 11 is a diagram showing a fourth display screen of the single cumulative dose distribution and the total cumulative dose distribution that are sequentially calculated during a radiation irradiating manipulation under execution.

FIG. 11 is a diagram showing a fourth display screen (entire and partial display screen) of the single cumulative dose distribution and the total cumulative dose distribution that are sequentially calculated during the radiation irradiating manipulation under execution.

A display screen D4 shown in FIG. 11 contains the single cumulative dose distribution and the total cumulative dose distribution, one of which is sequentially displayed in its entirety, and the other of which is sequentially displayed partially. For example, on the display screen D4, the entire single cumulative dose distribution is displayed while a part of the total cumulative dose distribution is displayed. The entire single cumulative dose distribution on the display screen D4 is sequentially updated. The update allows the operator to sequentially view the cumulative dose from the start of the radiation irradiating manipulation under execution to the present time. The part of the total cumulative dose distribution on the display screen D4 is sequentially updated. The update allows the operator to sequentially view the cumulative dose to the present time from the past radiation irradiating manipulations pertaining to the patient.

On the display screen D4 shown in FIG. 11, the entire single cumulative dose distribution is displayed while the part of the total cumulative dose distribution is displayed. Alternatively, the object to be displayed in its entirety and the object to be displayed partially may be replaced with each other. A configuration may be adopted that can freely switch between the entire display and the partial display.

Figure 12:
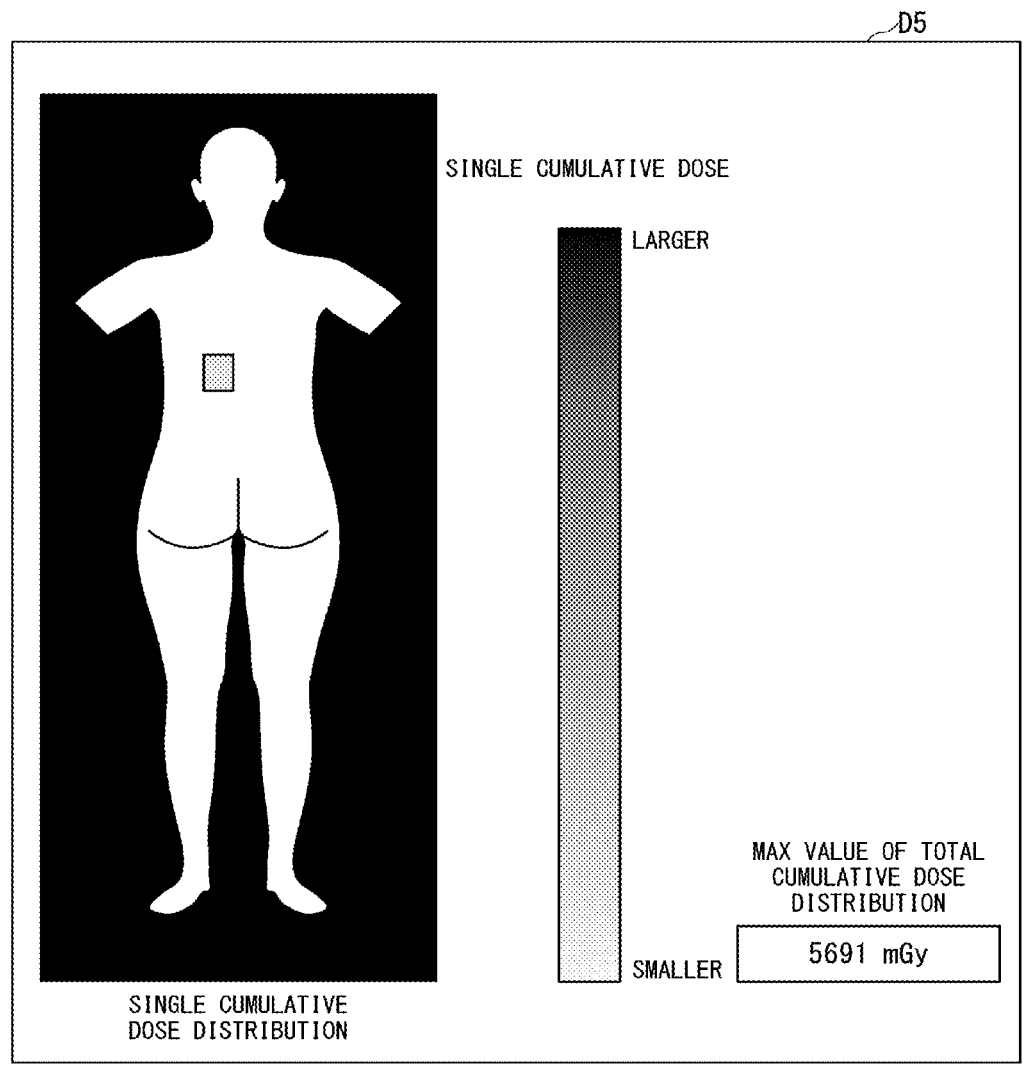
FIG. 12 is a diagram showing a fifth display screen of the single cumulative dose distribution and the total cumulative dose distribution that are sequentially calculated during a radiation irradiating manipulation under execution.

FIG. 12 is a diagram showing a fifth display screen (shaded and numeric display screen) of the single cumulative dose distribution and the total cumulative dose distribution that are sequentially calculated during the radiation irradiating manipulation under execution.

On the display screen D5 shown in FIG. 12, one of the single cumulative dose distribution and the total cumulative dose distribution is shaded and sequentially displayed, and the maximum value of the other distribution is sequentially displayed in a numeric value. For example, on the display screen D5, the shade according to the single cumulative dose distribution and the maximum value are displayed, the maximum value being among the total cumulative doses in the total cumulative dose distribution. The shade according to the single cumulative dose distribution on the display screen D5 is sequentially updated. The update allows the operator to sequentially view the cumulative dose from the start of the radiation irradiating manipulation under execution to the present time. The maximum value of the total cumulative doses on the display screen D5 is sequentially updated. The update allows the operator to sequentially view the maximum value of the cumulative dose to the present time from the past radiation irradiating manipulations pertaining to the patient.

On the display screen D5 shown in FIG. 12, the shaded single cumulative dose distribution is displayed while the maximum value of the total cumulative dose is numerically displayed. Alternatively, the object to be shaded and displayed and the object to be numerically displayed may be replaced with each other. A configuration may be adopted that can freely switch between the shaded display and the numeric display.

Figure 13:
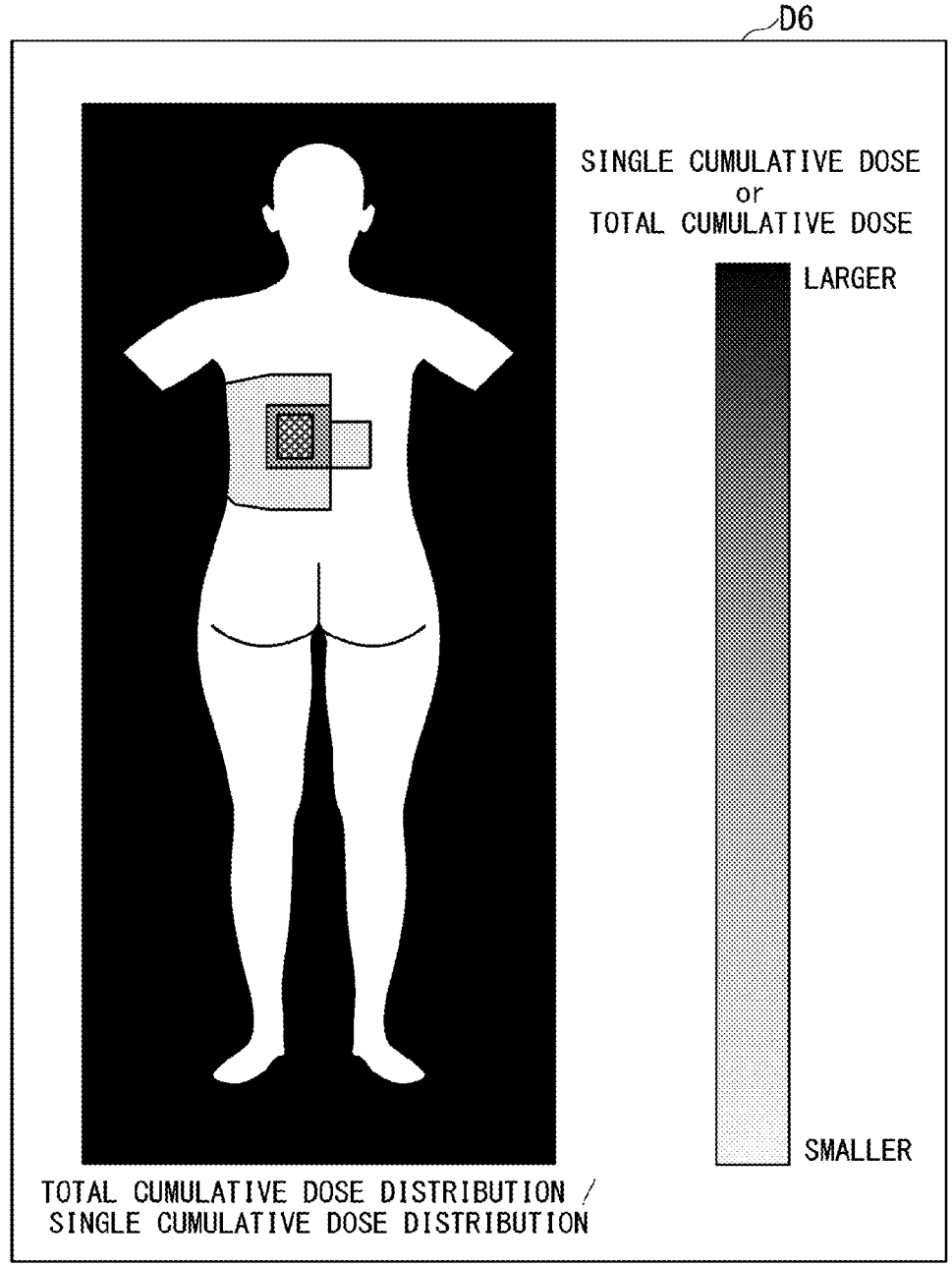
FIGS. 13 and 14 are diagrams showing a sixth display screen of the single cumulative dose distribution and the total cumulative dose distribution that are sequentially calculated during a radiation irradiating manipulation under execution.
Figure 14:
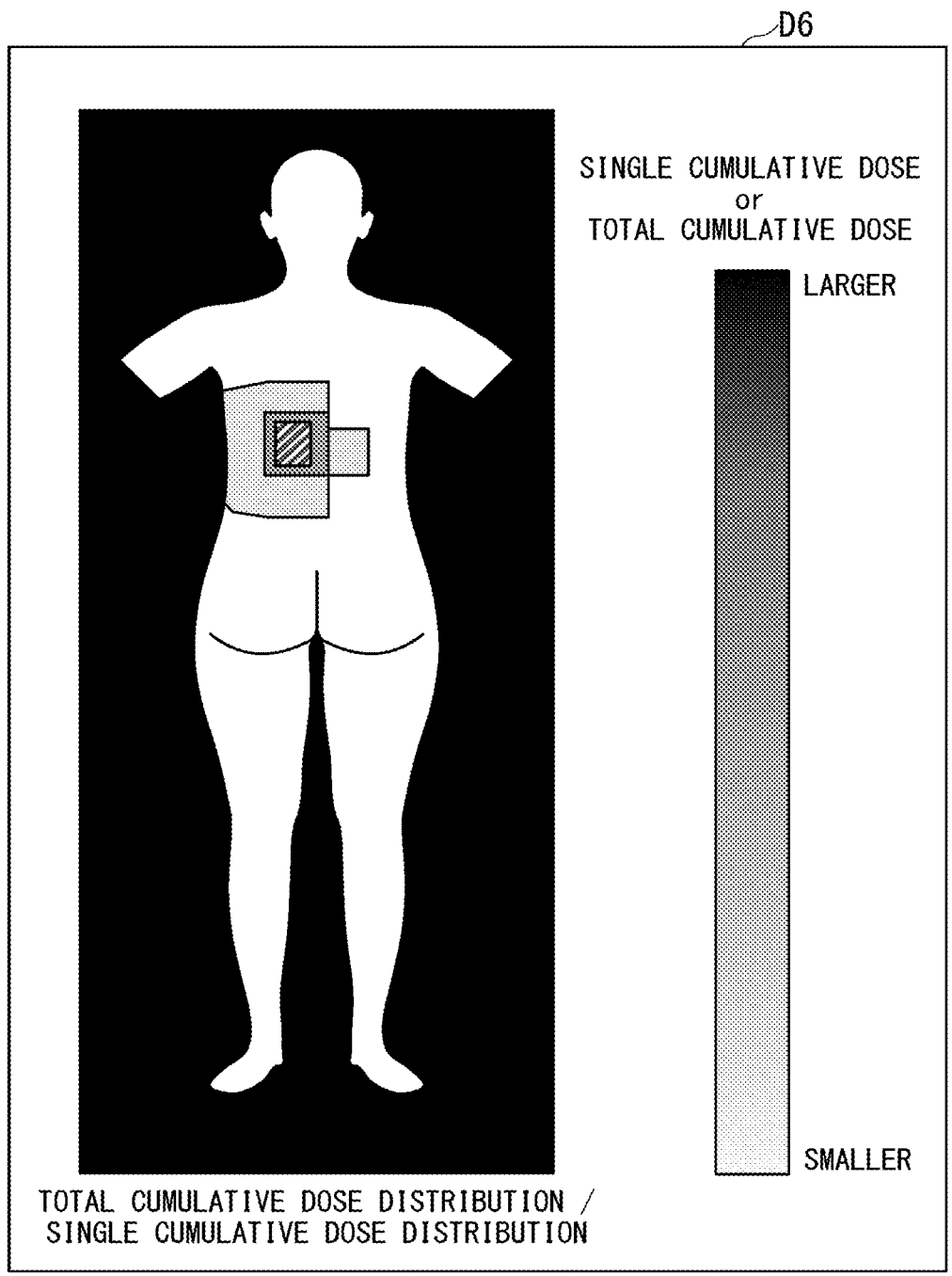

FIGS. 13 and 14 are diagrams showing a sixth display screen (overlaid display screens) of the single cumulative dose distribution and the total cumulative dose distribution that are sequentially calculated during the radiation irradiating manipulation under execution.

The display screen D6 shown in FIGS. 13 and 14 contains the single cumulative dose distribution and the total cumulative dose distribution which are sequentially displayed in different display patterns in an overlaid manner. On body surface portions having single cumulative doses higher than zero on the three-dimensional image (rendered image) of the single cumulative dose distribution, dots are set at intervals. The dots are represented by the attribute information on colors according to the degrees of the single cumulative doses on the dots (the average value of single cumulative doses on the dots). As with the display screen D6 shown in FIG. 13, dots assigned color attribute information on the basis of the single cumulative dose distribution are overlaid on the three-dimensional image of the total cumulative dose distribution, thereby allowing the single cumulative dose distribution and the total cumulative dose distribution to be displayed in an overlaid manner.

On the other hand, the body surface portions having single cumulative doses higher than zero on the three-dimensional image of the single cumulative dose distribution are hatched. The hatching is represented by the attribute information on colors according to the degrees of the single cumulative doses on the hatching (the average value of single cumulative doses on the hatching). As illustrated in the display screen D6 shown in FIG. 14, the hatching assigned color attribute information on the basis of the single cumulative dose distribution is overlaid on the three-dimensional image of the total cumulative dose distribution, thereby allowing the single cumulative dose distribution and the total cumulative dose distribution to be displayed in an overlaid manner.

The single cumulative dose distribution on the display screen D6 is sequentially updated. The update allows the operator to sequentially view the cumulative dose from the start of the radiation irradiating manipulation under execution to the present time. The total cumulative dose distribution on the display screen D6 is sequentially updated. The update allows the operator to sequentially view the cumulative dose to the present time from the past radiation irradiating manipulations pertaining to the patient.

Returning to the description with reference to FIG. 5, after the radiation irradiating manipulation by the radiation irradiation executing function 115 is finished, the cumulative dose distribution registering function 117 assigns the patient identifying information and the execution time information to the cumulative dose distribution (single cumulative dose distribution) calculated by the single cumulative dose distribution calculating function 116a of the sequential cumulative dose distribution calculating function 116, and registers the distribution in the cumulative dose distribution DB 17.

The radiation irradiating apparatus 10 according to the present embodiment effectively displays, on the display 14, at least one of the single cumulative dose distribution and the total cumulative dose distribution pertaining to the patient during application of the radiation irradiating manipulation to the patient, thereby allowing the operator, who is a medical doctor or a medical technician, to easily monitor the single cumulative dose distribution and the total cumulative dose distribution during the application of the radiation irradiating manipulation to the patient.

The radiation irradiating apparatus 10 according to the present embodiment effectively displays, on the display 14, at least one of the single cumulative dose distribution and the total cumulative dose distribution during application of the radiation irradiating manipulation to the patient, thereby allowing the operator to easily determine an appropriate radiation irradiating direction so as to prevent portions having been irradiated with radiation from being further irradiated, during the application of the radiation irradiating manipulation to the patient. Consequently, the radiation damage to the patient can be alleviated. The radiation irradiating apparatus 10 according to the present embodiment allows the operator to perform the radiation irradiating manipulation while verifying whether the application of the radiation during their radiation irradiating manipulation to the patient is appropriate or not through the display 14.

(Radiation Dose Management System)

Figure 15:
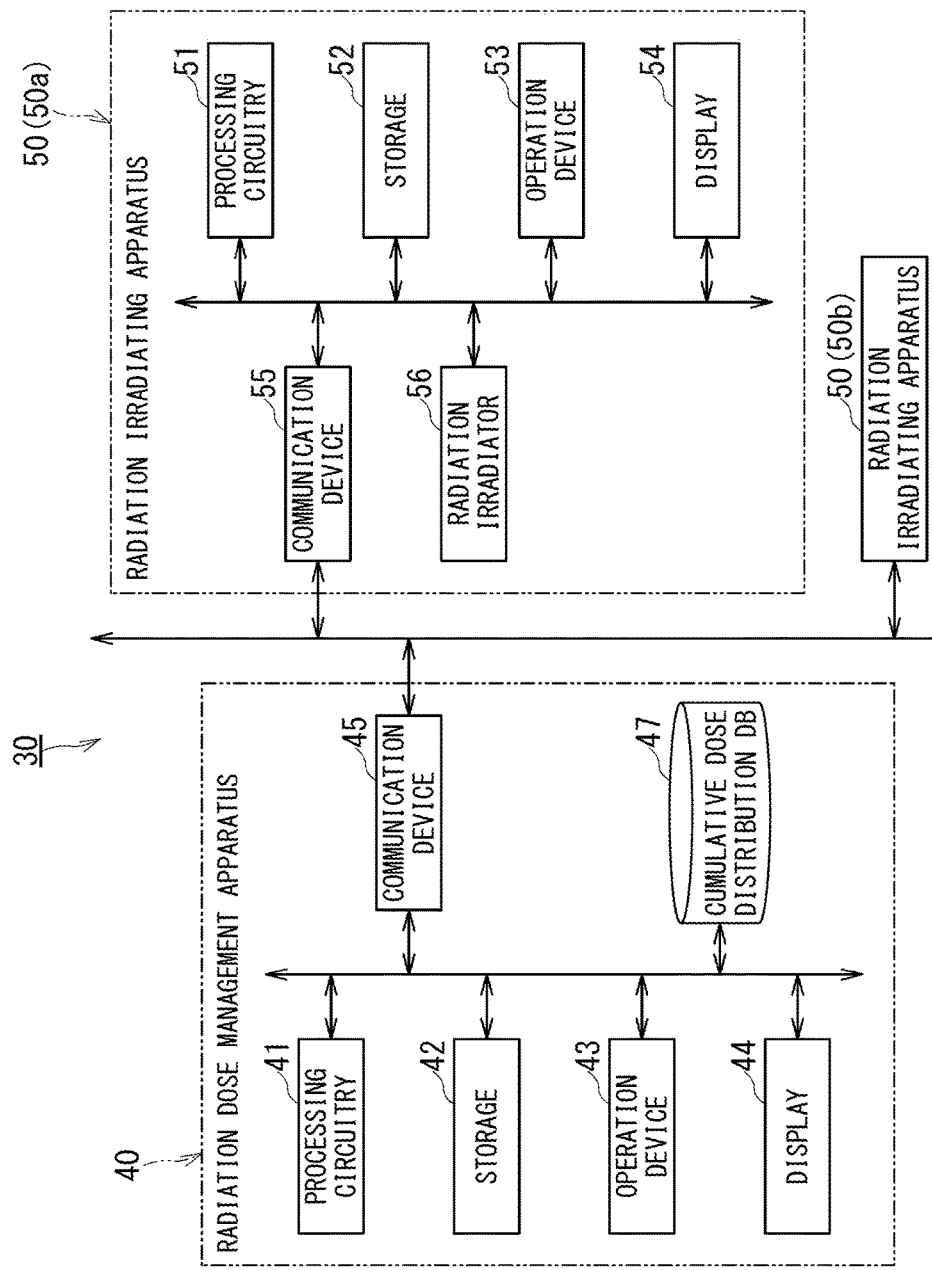
FIG. 15 is a schematic diagram showing a configuration of a radiation dose management system according to a present embodiment.

FIG. 15 is a schematic diagram showing a configuration of a radiation dose management system according to a present embodiment.

FIG. 15 shows the radiation dose management system 30 according to the present embodiment. The radiation dose management system 30 includes a radiation dose management apparatus 40, and multiple radiation irradiating apparatuses 50 (radiation irradiating apparatuses 50a, 50b, . . . ). The radiation irradiating apparatuses 50 may be, for example, any of radiation diagnostic apparatuses (radiation exam apparatuses), such as X-ray diagnostic apparatuses and X-ray CT apparatuses, and radiation therapeutic apparatuses, such as gamma knives.

The radiation dose management apparatus 40 has a configuration of a typical computer. The radiation dose management apparatus 40 roughly includes basic hardware, which is a processing circuitry 41, a storage 42, an operation device 43, a display 44 and a communication device 45, and a cumulative dose distribution DB 47. The processing circuitry 41 is mutually connected to each of the hardware configuration elements, which configure the radiation dose management apparatus 40, via a bus as a common signal transmission path.

The elements, from the processing circuitry 41 to the communication device 45, have the same configurations and functions as those of the respective elements, from the processing circuitry 11 to the communication device 15, shown in FIG. 1. Consequently, the description thereof is omitted.

As with the cumulative dose distribution DB 17 shown in FIG. 1, the cumulative dose distribution DB 47 is a storage that includes an HDD and a memory. The cumulative dose distribution DB 47 can store data on the cumulative dose distribution that represents the three-dimensional distribution of cumulative doses (mGy) accompanied by any of patient identifying information (patient ID) for identifying a patient, execution time information on past radiation irradiating manipulations, and apparatus identifying information for identifying a radiation irradiating apparatus among the radiation irradiating apparatuses having performed the radiation irradiating manipulation (shown in FIG. 16). The cumulative dose distribution is typically generated with respect to each radiation irradiating manipulation.

Unlike the cumulative dose distribution DB 17 shown in FIG. 1, the cumulative dose distribution DB 47 can store data on multiple cumulative dose distributions that have been calculated by the respective radiation irradiating apparatuses 50 and transmitted from these apparatuses 50.

Figure 16:
FIG. 16 is a diagram showing an example of data on a cumulative dose distribution.
Figure 16:
Figure 16:
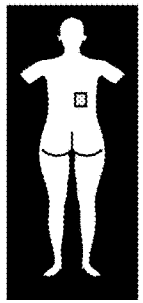
Figure 16:

FIG. 16 is a diagram showing an example of data on the cumulative dose distribution.

As shown in FIG. 16, the cumulative dose distribution DB (shown in FIG. 15) can store multiple cumulative dose distributions where cumulative doses in a human body model coordinate system are associated with respective body surface positions of the human body model. Each cumulative dose distribution is accompanied by the patient identifying information contained in the patient information, the execution time information, and the apparatus identifying information. FIG. 16 shows the case where mapping of the cumulative doses to the body surface positions of the human body model is stored as the cumulative dose distribution. Alternatively, data on the human body model, and the cumulative doses on the body surface positions may be separately stored.

Returning to the description with reference to FIG. 15, each of the radiation irradiating apparatuses 50 has a configuration of a typical computer. Each of the radiation irradiating apparatuses 50 roughly includes basic hardware, which is processing circuitry 51, a storage 52, an operation device 53, a display 54 and a communication device 55, and a radiation irradiator 56. The processing circuitry 51 is mutually connected to each of the hardware configuration elements, which configure the radiation irradiating apparatuses 50, via a bus as a common signal transmission path.

The elements, from the processing circuitry 51 to the communication device 55, have the same configurations and functions as those of the respective elements, from the processing circuitry 11 to the communication device 15, shown in FIG. 1. Consequently, the description thereof is omitted.

The radiation irradiator 56 has a configuration equivalent to the configuration of the radiation irradiator 16 shown in FIG. 1. The radiation irradiator 56 is a device that irradiates a patient with radiation under control of the processing circuitry 51. In the case where any of the radiation irradiating apparatuses 50 is an X-ray diagnostic apparatus, the radiation irradiator 56 of this radiation irradiating apparatus includes typical structures, such as a high voltage generator, an X-ray source, an X-ray detector, and a bed. In the case where any of the radiation irradiating apparatuses 50 is an X-ray CT apparatus, the radiation irradiator 56 of the radiation irradiating apparatus includes typical structures, such as a high voltage generator, an X-ray source, an X-ray detector, a rotation unit, and a bed. In the case where any of the radiation irradiating apparatuses is a radiation therapeutic apparatus, the radiation irradiator 56 of this radiation irradiating apparatus includes typical structures, such as a high voltage generator, a radiation source, a rotation unit, and a bed.

A set of FIGS. 17A and 17B is a block diagram showing functions of the radiation dose management system 30 according to the present embodiment.

The processing circuitry 41 included in the radiation dose management system 30 according to the present embodiment executes the programs to thereby cause the radiation dose management apparatus 40 to function as a condition receiving function 411, a past cumulative dose distribution acquiring function 412, a past added dose distribution calculating function 413, a past added dose distribution transmitting function 414, a cumulative dose distribution receiving function 415, and a cumulative dose distribution registering function 416. The description is made assuming that the functions 411 to 416 function as software. Alternatively, all or some of the functions 411 to 416 may be implemented as hardware in the radiation dose management apparatus 40.

The condition receiving function 411 receives the patient identifying information (patient ID) that has been set by a specific radiation irradiating apparatus 50a among the radiation irradiating apparatuses 50 and transmitted from this apparatus 50a.

The past cumulative dose distribution acquiring function 412 has a function equivalent to that of the past cumulative dose distribution acquiring function 113 shown in FIG. 4. That is, the past cumulative dose distribution acquiring function 412 acquires (reads), from the cumulative dose distribution DB 47, the past cumulative dose distributions associated with the patient identifying information received by the condition receiving function 411. When the condition receiving function 411 sets the period condition, the past cumulative dose distribution acquiring function 412 acquires, from the cumulative dose distribution DB 47, the cumulative dose distributions associated with the patient identifying information received by the condition receiving function 411 and with the execution time information within the range of the period condition. Furthermore, when the condition receiving function 411 sets an apparatus condition, the past cumulative dose distribution acquiring function 412 acquires, from the cumulative dose distribution DB 47, the cumulative dose distributions associated with the patient identifying information received by the condition receiving function 411 and with the apparatus identifying information encompassed by the apparatus condition.

The past added dose distribution calculating function 413 has a function equivalent to that of the past added dose distribution calculating function 114 shown in FIG. 4. That is, when the past cumulative dose distributions are acquired by the past cumulative dose distribution acquiring function 412, the past added dose distribution calculating function 413 aligns the past cumulative dose distributions and adds (or totalizes) the distributions with respect to each body surface position of the human body model, thereby calculating the data on the past added dose distribution pertaining to the past radiation irradiating manipulations.

That is, when the past cumulative dose distributions are received by the past cumulative dose distribution acquiring function 412, the past added dose distribution calculating function 413 adds the past cumulative doses with respect to each body surface position, thereby calculating the data on the past added dose distribution pertaining to the past radiation irradiating manipulations. In the case where one past cumulative dose distribution is acquired by the past cumulative dose distribution acquiring function 412, the past added dose distribution calculating function 413 is unnecessary. Here, the example of the data on the past added dose distribution is equivalent to that shown in FIG. 6.

Alternatively, the past added dose distribution calculating function 413 may be included in each of the radiation irradiating apparatuses 50.

The past added dose distribution transmitting function 414 transmits the past added dose distribution calculated by the past added dose distribution calculating function 413, to the radiation irradiating apparatus 50a having transmitted the patient identifying information.

The cumulative dose distribution receiving function 415 receives the cumulative dose distribution that has been calculated by the radiation irradiating apparatus 50a, which has transmitted the patient identifying information, and been transmitted from this apparatus 50a.

The cumulative dose distribution registering function 416 has a function equivalent to that of the cumulative dose distribution registering function 117 shown in FIG. 4. That is, after the radiation irradiating manipulation by the radiation irradiating apparatus 50a is finished, the cumulative dose distribution registering function 416 assigns the patient identifying information, the execution time information and the apparatus identifying information to the cumulative dose distribution (single cumulative dose distribution) calculated by the radiation irradiating apparatus 50a, and registers the distribution in the cumulative dose distribution DB 47.

The processing circuitry 51 included in the radiation dose management system 30 according to the present embodiment executes the programs to thereby cause each of the radiation irradiating apparatuses 50 to function as an operation assisting function 511, a condition setting function 512, a condition transmitting function 513, a past added dose distribution receiving function 514, a radiation irradiation executing function 515, a sequential cumulative dose distribution calculating function 516, and a cumulative dose distribution transmitting function 517. The description is made assuming that the functions 511 to 517 function as software. Alternatively, all or some of the functions 511 to 517 may be implemented as hardware in each of the radiation irradiating apparatuses 50.

The operation assisting function 511 has a function equivalent to the operation assisting function 111 shown in FIG. 4. That is, the operation assisting function 511 functions as an interface, such as GUI, that mediates the functions 512 to 517 and the operation device 53 and the display 54.

The condition setting function 512 has a function equivalent to the condition setting function 112 shown in FIG. 4. That is, the condition setting function 512 sets the patient identifying information (patient ID) based on an operation at the operation device 53 through the operation assisting function 511. The patient ID is used for acquiring the past cumulative dose distributions pertaining to the patient subjected to the radiation irradiating manipulation. In addition, the condition setting function 512 may set a period condition for acquiring only the cumulative dose distributions in a specific period and the apparatus condition for acquiring only the cumulative dose distribution generated through the radiation irradiating manipulation by the specific radiation irradiating apparatus, among the entire past cumulative dose distributions pertaining to the patient subjected to the radiation irradiating manipulation.

The condition transmitting function 513 transmits the patient identifying information set by the condition setting function 512 to the condition receiving function 411 of the radiation dose management apparatus 40.

The past added dose distribution receiving function 514 receives the past added dose distribution transmitted from the past added dose distribution transmitting function 414 of the radiation dose management apparatus 40.

The radiation irradiation executing function 515 has a function equivalent to that of the radiation irradiation executing function 115 shown in FIG. 4. That is, the radiation irradiation executing function 515 applies a radiation irradiating manipulation to the patient associated with the patient identifying information set by the condition setting function 512. Here, in the case where any of the radiation irradiating apparatuses 50 is an X-ray diagnostic apparatus or an X-ray CT apparatus, the radiation irradiation executing function 515 of this radiation irradiating apparatus controls the operation of the radiation irradiator 56 to collect an image pertaining to detection portion of the patient while emitting radiation. In the case where any of the radiation irradiating apparatuses 50 is a radiation therapeutic apparatus, the radiation irradiation executing function 515 of this radiation irradiating apparatus controls the operation of the radiation irradiator 56 to irradiate a therapy target portion of the patient.

The sequential cumulative dose distribution calculating function 516 has a function equivalent to that of the sequential cumulative dose distribution calculating function 116 shown in FIG. 4. That is, during execution of the radiation irradiating manipulation by the radiation irradiation executing function 515, the sequential cumulative dose distribution calculating function 516 cumulates the exposure dose until the present time, thereby sequentially calculating the cumulative dose. The sequential cumulative dose distribution calculating function 516 sequentially calculates the cumulative dose distribution that associates the cumulative doses with the body surface positions of the human body model.

The body surface position of the patient in the real coordinate system is coordinate-transformed into the corresponding body surface position in the human body model in the model coordinate system. This transformation allows the cumulative dose pertaining to the body surface position of the patient in the real coordinate system to be considered as the cumulative dose on the corresponding body surface position of the human body model. The sequential cumulative dose distribution calculating function 516 includes a single cumulative dose distribution calculating function 516a, and a total cumulative dose distribution calculating function 516b.

The single cumulative dose distribution calculating function 516a has a function equivalent to that of the single cumulative dose distribution calculating function 116a. That is, the single cumulative dose distribution calculating function 516a sequentially calculates, as the single cumulative dose distribution, the cumulative dose distribution from the start of the radiation irradiating manipulation under execution to the present time during execution of the radiation irradiating manipulation. The single cumulative dose distribution associates the cumulative doses from the start of the radiation irradiating manipulation under execution to the present time with the body surface positions of the human body model.

The total cumulative dose distribution calculating function 516b sequentially adds the single cumulative dose distribution calculated by the single cumulative dose distribution calculating function 516a to the past added dose distribution received by the past added dose distribution receiving function 514, during execution of the radiation irradiating manipulation. The total cumulative dose distribution calculating function 516b sequentially calculates the total cumulative dose to the present time from the start of the radiation irradiating manipulation pertaining to the latest cumulative dose distribution among the past cumulative dose distributions. The total cumulative dose distribution associates, with the body surface positions of the human body model, the total cumulative doses to the present time from the start of the radiation irradiating manipulation pertaining to the latest cumulative dose distribution among the past cumulative dose distributions.

When the one past cumulative dose distribution is acquired by the past cumulative dose distribution acquiring function 412, the total cumulative dose distribution calculating function 516b sequentially adds the single cumulative dose distribution calculated by the single cumulative dose distribution calculating function 516a to one past cumulative dose distribution during execution of the radiation irradiating manipulation. The total cumulative dose distribution calculating function 516b calculates the total cumulative dose to the present time from the start of the radiation irradiating manipulation pertaining to the one past cumulative dose distribution.

The sequential cumulative dose distribution calculating function 516 sequentially displays, on the display 54 (corresponding to the display 14 in FIG. 2), the single cumulative dose distribution and the total cumulative dose distribution through the operation assisting function 511 during execution of the radiation irradiating manipulation (FIGS. 8 and 10 to 14). Alternatively, the sequential cumulative dose distribution calculating function 516 switches between sequential display of the single cumulative dose distribution on the display 54 through the operation assisting function 511 and the sequential display of the total cumulative dose distribution on the display 54 through the operation assisting function 511 during execution of the radiation irradiating manipulation (FIG. 9).

The cumulative dose distribution transmitting function 517 transmits, after the radiation irradiating manipulation by the radiation irradiation executing function 515 is finished, the cumulative dose distribution (single cumulative dose distribution) calculated by the single cumulative dose distribution calculating function 516a of the sequential cumulative dose distribution calculating function 516 together with the patient identifying information, the execution time information and the apparatus identifying information, to the cumulative dose distribution receiving function 415 of the radiation dose management apparatus 40.

Subsequently, the operations of the radiation dose management system 30 according to the present embodiment are described with reference to FIGS. 15 and 18.

A set of FIGS. 18A and 18B is a flowchart showing operations of the radiation dose management system 30 according to the present embodiment.

One radiation irradiating apparatus 50a among the radiation irradiating apparatuses 50 in the radiation dose management system 30 sets the patient identifying information "Patient P1" for acquiring the past cumulative dose distributions pertaining to the patient subjected to the radiation irradiating manipulation (step ST1). In addition, step ST1 may set a period condition for acquiring only the cumulative dose distributions in a specific period and the apparatus condition for acquiring only the cumulative dose distribution generated by the radiation irradiating manipulation by the specific radiation irradiating apparatus, among all the past cumulative dose distributions pertaining to the patient subjected to the radiation irradiating manipulation.

The radiation irradiating apparatus 50a transmits the patient identifying information "Patient P1" set in step ST1 to the radiation dose management apparatus 40 (step ST2).

The radiation dose management apparatus 40 receives the patient identifying information "Patient P1" transmitted in step ST2, and acquires the past cumulative dose distributions associated with the received patient identifying information "Patient P1" from the cumulative dose distribution DB 47 (shown in FIG. 16) (step ST3).

When the past cumulative dose distributions are acquired in step ST3, the radiation dose management apparatus 40 aligns and adds the past cumulative dose distributions, thereby calculating the data on a past added dose distribution pertaining to the past radiation irradiating manipulations (step ST4).

The radiation dose management apparatus 40 transmits the past added dose distribution calculated in step ST4 to radiation irradiating apparatus 50a (step ST5).

The radiation irradiating apparatus 50a receives the past added dose distribution transmitted in step ST5, and starts applying the radiation irradiating manipulation to the patient associated with the patient identifying information "Patient P1" set in step ST1 (step ST6).

The radiation irradiating apparatus 50a calculates the cumulative dose distribution as the single cumulative dose distribution during execution of the radiation irradiating manipulation, and displays the distribution on the display 54

(step ST7). At the same time, the radiation irradiating apparatus 50a adds the single cumulative dose distribution calculated in step ST7 to the past added dose distribution received in step ST6 during execution of the radiation irradiating manipulation, thus calculating the total cumulative dose distribution and displaying the calculated distribution on the display 54 (corresponding to display 14 shown in FIG. 2) (step ST8). Display screens in steps ST7 and ST8 are shown in FIGS. 8 to 14.

The single cumulative dose distribution and the total cumulative dose distribution in steps ST7 and ST8 are repeatedly displayed until the radiation irradiating manipulation under execution is finished.

After the radiation irradiating manipulation started in step ST6 is finished, the radiation irradiating apparatus 50a assigns the patient identifying information, the execution time information and the apparatus identifying information to the cumulative dose distribution (single cumulative dose distribution) calculated in step ST7, and transmits the distribution to the radiation dose management apparatus 40 (step ST9).

The radiation dose management apparatus 40 receives the cumulative dose distribution transmitted in step ST9, and registers the received cumulative dose distribution in the cumulative dose distribution DB 47 (step ST10).

Next, at a timing after step ST1, another radiation irradiating apparatus 50b among the radiation irradiating apparatuses 50 in the radiation dose management system 30 sets the patient identifying information "Patient P1" for acquiring the past cumulative dose distributions pertaining to the patient subjected to the radiation irradiating manipulation (step ST11). In addition, step ST11 may set a period condition for acquiring only the cumulative dose distributions in a specific period among all the past cumulative dose distributions pertaining to the patient subjected to the radiation irradiating manipulation.

The radiation irradiating apparatus 50b transmits the patient identifying information "Patient P1" set in step ST11 to the radiation dose management apparatus 40 (step ST12).

The radiation dose management apparatus 40 receives the patient identifying information "Patient P1" transmitted in step ST12, and acquires the past cumulative dose distributions associated with the received patient identifying information "Patient P1" from the cumulative dose distribution DB 47 (step ST13). Here, the patient identifying information "Patient P1" received in step ST3 coincides with the patient identifying information "Patient P1" received in step ST13. Consequently, the past cumulative dose distribution acquired in step ST13 contains the cumulative dose distribution registered in step ST10.

When multiple past cumulative dose distributions are acquired in step ST13, the radiation dose management apparatus 40 aligns and adds the past cumulative dose distributions, thereby calculating the data on a past added dose distribution pertaining to the past radiation irradiating manipulations (step ST14).

The radiation dose management apparatus 40 transmits the past added dose distribution calculated in step ST14 to radiation irradiating apparatus 50b (step ST15).

The radiation irradiating apparatus 50b receives the past added dose distribution transmitted in step ST15, and starts applying the radiation irradiating manipulation to the patient associated with the patient identifying information "Patient P1" set in step ST11 (step ST16).

The radiation irradiating apparatus 50b calculates the cumulative dose distribution as the single cumulative dose distribution during execution of the radiation irradiating manipulation, and displays the distribution on the display 54 (step ST17). At the same time, the radiation irradiating apparatus 50b adds the single cumulative dose distribution calculated in step ST17 to the past added dose distribution received in step ST16 during execution of the radiation irradiating manipulation, thus calculating the total cumulative dose distribution and displaying the calculated distribution on the display 54 (display 14 shown in FIG. 2) (step ST18). Display screens in steps ST17 and ST18 are shown in FIGS. 8 to 14.

The single cumulative dose distribution and the total cumulative dose distribution in steps ST17 and ST18 are repeatedly displayed until the radiation irradiating manipulation under execution is finished.

After the radiation irradiating manipulation started in step ST16 is finished, the radiation irradiating apparatus 50b assigns the patient identifying information, the execution time information and the apparatus identifying information to the cumulative dose distribution (single cumulative dose distribution) calculated in step ST17, and transmits the distribution to the radiation dose management apparatus 40 (step ST19).

The radiation dose management apparatus 40 receives the cumulative dose distribution transmitted in step ST19, and registers the received cumulative dose distribution in the cumulative dose distribution DB 47 (step ST20).

The radiation dose management system 30 according to the present embodiment effectively displays, on the display 54, at least one of the single cumulative dose distribution and the total cumulative dose distribution during application of the radiation irradiating manipulation to the patient, thereby allowing the operator, who is a medical doctor or a medical technician, to easily monitor the single cumulative dose distribution and the total cumulative dose distribution pertaining to the patient during the application of the radiation irradiating manipulation to the patient.

The radiation dose management system 30 according to the present embodiment effectively displays, on the display 54, at least one of the single cumulative dose distribution and the total cumulative dose distribution during application of the radiation irradiating manipulation to the patient, thereby allowing the operator to easily determine an appropriate radiation irradiating direction so as to prevent portions having been irradiated with radiation from being further irradiated, during the application of the radiation irradiating manipulation to the patient. Consequently, the radiation damage to the patient can be alleviated. The radiation dose management system 30 according to the present embodiment allows the operator to perform the radiation irradiating manipulation while verifying whether the application of the radiation during their radiation irradiating manipulation to the patient is appropriate or not through the display 54.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. A radiation irradiating apparatus, comprising:
   processing circuitry configured to acquire a past spatial cumulative dose distribution associated with patient identifying information, from a memory storing spatial cumulative dose distributions;

cause a radiation irradiator apparatus that emits radiation to irradiate the radiation to a patient associated with the patient identifying information;

calculate, during the irradiation of the radiation, a first spatial cumulative dose distribution and a second spatial cumulative dose distribution, the second spatial cumulative dose distribution being generated by adding the first spatial cumulative dose distribution to the past spatial cumulative dose distribution; and display, on a display during the irradiation of the radiation, at least one of the first and second spatial cumulative dose distributions, wherein each of the spatial cumulative dose distributions is generated by coordinate-transforming each position of a spatial cumulative dose distribution in a real coordinate system to a corresponding position of a spatial human body model or of volume data of the patient.

2. The radiation irradiating apparatus according to claim 1, wherein
the radiation is X-rays, and
the processing circuitry is further configured to:
sequentially generate each of fluoroscopic images based on the X-rays having passed through the patient; and
sequentially display, on the display, a spatial distribution that is at least one of the first and second spatial cumulative dose distributions, and display, on the display, the fluoroscopic images as a moving image.

3. The radiation irradiating apparatus according to claim 1, wherein the processing circuitry is further configured to register the first spatial cumulative dose distribution in the memory.

4. The radiation irradiating apparatus according to claim 1, wherein the processing circuitry is further configured to:
align, when a plurality of past spatial cumulative dose distributions are acquired as the past spatial cumulative dose distribution, the past spatial cumulative dose distributions, and add the aligned spatial distributions with respect to body surface positions of the spatial human body model to calculate a past added spatial dose distribution; and
add the first spatial cumulative dose distribution to the past added spatial dose distribution during the radiation irradiation to calculate the second spatial cumulative dose distribution.

5. The radiation irradiating apparatus according to claim 1, wherein the processing circuitry is further configured to display the first and second spatial cumulative dose distributions in a juxtaposed manner.

6. The radiation irradiating apparatus according to claim 1, wherein the processing circuitry is further configured to switchably display, on the display, the first and second spatial cumulative dose distributions.

7. The radiation irradiating apparatus according to claim 1, wherein the processing circuitry is further configured to zoom in and display one of the first and second spatial cumulative dose distributions, while zooming out and displaying the other distribution.

8. The radiation irradiating apparatus according to claim 1, wherein the processing circuitry is further configured to sequentially and entirely display, on the display, one of the first and second spatial cumulative dose distributions, while sequentially and partially displaying the other distribution on the display.

9. The radiation irradiating apparatus accord ink to claim 1, wherein the processing circuitry is further configured to sequentially display, on the display, one of the first and second spatial cumulative dose distributions in a shaded manner, while sequentially displaying the other distribution on the display in a numeric value.

10. The radiation irradiating apparatus according to claim 1, wherein the processing circuitry is further configured to sequentially display, on the display, the first and second spatial cumulative dose distributions in different display patterns in an overlaid manner.

11. A radiation dose management system, comprising:
processing circuitry configured to
acquire a past spatial cumulative dose distribution associated with required patient identifying information, from a memory storing a plurality of spatial cumulative dose distributions by a plurality of radiation irradiating apparatuses performing radiation irradiations;
cause a radiation irradiator apparatus that emits radiation to irradiate the radiation to a patient associated with the patient identifying information;
calculate, during the irradiation of the radiation, a first spatial cumulative dose distribution and a second spatial cumulative dose distribution, the second spatial cumulative dose distribution being generated by adding the first spatial cumulative dose distribution to the past spatial cumulative dose distribution; and
display, on a display during the irradiation of the radiation, at least one of the first and second spatial cumulative dose distributions,
wherein each of the spatial cumulative dose distributions is generated by coordinate-transforming each position of a spatial cumulative dose distribution in a real coordinate system to a corresponding position of a spatial human body model or of volume data of the patient.

12. The radiation irradiating apparatus according to claim 1, wherein
each of the spatial cumulative dose distributions is a distribution generated by mapping cumulative doses to body surface positions of the spatial human body model or of volume data of the patient.

13. The radiation irradiating apparatus of claim 1, wherein the calculated first spatial cumulative dose distribution corresponds to a spatial cumulative dose distribution acquired during the irradiation of the radiation to the patient.

* * * * *